United States Patent
Chien et al.

(10) Patent No.: US 9,936,961 B2
(45) Date of Patent: Apr. 10, 2018

(54) SURGICAL TOOL WITH FEEDBACK

(71) Applicant: DePuy Synthes Products, LLC, Raynham, MA (US)

(72) Inventors: Dennis Chien, West Chester, PA (US); Michael O'Neil, Raynham, MA (US); Mark Hall, Raynham, MA (US); Riley Hawkins, Raynham, MA (US); Roman Lomeli, Raynham, MA (US)

(73) Assignee: DEPUY SYNTHES PRODUCTS, INC., Raynham, MA (US)

( * ) Notice: Subject to any disclaimer, the term of this patent is extended or adjusted under 35 U.S.C. 154(b) by 742 days.

(21) Appl. No.: 14/498,658

(22) Filed: Sep. 26, 2014

(65) Prior Publication Data
US 2016/0089154 A1 Mar. 31, 2016

(51) Int. Cl.
A61B 17/16 (2006.01)
A61B 90/57 (2016.01)
A61B 17/00 (2006.01)
A61B 90/00 (2016.01)

(52) U.S. Cl.
CPC .......... *A61B 17/1626* (2013.01); *A61B 17/16* (2013.01); *A61B 17/1671* (2013.01); *A61B 90/57* (2016.02); *A61B 2017/00017* (2013.01); *A61B 2017/00022* (2013.01); *A61B 2017/00075* (2013.01); *A61B 2017/00128* (2013.01); *A61B 2017/00199* (2013.01); *A61B 2017/00221* (2013.01); *A61B 2090/3983* (2016.02)

(58) Field of Classification Search
CPC ...... A61B 17/16–17/1693; A61B 2017/00115; A61B 2017/00119; A61B 2017/00123; A61B 2017/00199; A61B 2017/0021

USPC ...................................................... 606/79–80
See application file for complete search history.

(56) References Cited

U.S. PATENT DOCUMENTS

| | | | |
|---|---|---|---|
| 6,433,464 B2 | 8/2002 | Jones | |
| 6,666,875 B1 | 12/2003 | Sakurai et al. | |
| 8,221,398 B2 * | 7/2012 | Isobe | A61B 17/1626 606/1 |
| 8,348,950 B2 | 1/2013 | Assell et al. | |
| 8,442,621 B2 * | 5/2013 | Gorek | A61B 17/7091 600/424 |
| 8,568,317 B1 * | 10/2013 | Gharib | A61B 8/0875 600/437 |
| 8,579,926 B2 | 11/2013 | Pintor et al. | |
| 8,636,736 B2 | 1/2014 | Yates et al. | |
| 8,690,888 B2 * | 4/2014 | Stein | A61B 17/025 606/102 |

(Continued)

FOREIGN PATENT DOCUMENTS

| | | |
|---|---|---|
| WO | 2013/134652 | 9/2013 |
| WO | 2013/177389 | 11/2013 |

OTHER PUBLICATIONS

International Search Report and Written Opinion (PCT/US2015/052177); dated Jan. 5, 2016.

*Primary Examiner* — Eric S Gibson
(74) *Attorney, Agent, or Firm* — Dunlap Codding, P.C.

(57) ABSTRACT

Surgical feedback systems and methods include a surgical tool having a functional tool and a handle for manipulation by a surgeon in a surgical environment. At least one sensor connected to the surgical tool generates a signal indicative of an acoustic signal and/or a vibration signal generated by the functional tool. The signal may be modified and supplied to an output device.

17 Claims, 13 Drawing Sheets

(56) References Cited

U.S. PATENT DOCUMENTS

| | | | |
|---|---|---|---|
| 8,746,530 B2 | 6/2014 | Giordano et al. | |
| 8,749,116 B2 * | 6/2014 | Messerly | A61B 17/320092 310/315 |
| 8,752,747 B2 * | 6/2014 | Shelton, IV | A61B 17/072 227/175.1 |
| 8,758,342 B2 | 6/2014 | Bales et al. | |
| 8,763,879 B2 | 7/2014 | Shelton, IV et al. | |
| 8,773,001 B2 | 7/2014 | Wiener et al. | |
| 2001/0039419 A1 * | 11/2001 | Francischelli | A61B 18/1442 606/42 |
| 2003/0078495 A1 * | 4/2003 | Goodwin | A61B 8/0841 600/424 |
| 2004/0028118 A1 * | 2/2004 | Sidoni | G01K 1/143 374/208 |
| 2005/0116673 A1 * | 6/2005 | Carl | A61B 17/1626 318/432 |
| 2006/0241628 A1 * | 10/2006 | Parak | A61B 17/1626 606/80 |
| 2008/0183188 A1 | 7/2008 | Carls et al. | |
| 2008/0249467 A1 * | 10/2008 | Burnett | A61B 1/313 604/117 |
| 2009/0149865 A1 * | 6/2009 | Schmitz | A61B 17/1659 606/114 |
| 2009/0245956 A1 * | 10/2009 | Apkarian | A61B 17/1626 408/1 R |
| 2010/0114184 A1 * | 5/2010 | Degtyar | A61B 17/1659 606/86 R |
| 2011/0082459 A1 * | 4/2011 | Aravot | A61B 17/1691 606/79 |
| 2011/0119224 A1 * | 5/2011 | Mangione-Smith | A61B 6/12 706/52 |
| 2012/0078278 A1 | 3/2012 | Bales, Jr. et al. | |
| 2012/0120384 A1 * | 5/2012 | Barrett | A61M 1/36 356/41 |
| 2012/0154789 A1 * | 6/2012 | Barrett | A61B 5/14535 356/41 |
| 2013/0012975 A1 * | 1/2013 | Schmitz | A61B 17/16 606/179 |
| 2013/0046292 A1 | 2/2013 | Janssen et al. | |
| 2013/0053851 A1 * | 2/2013 | Schmitz | A61B 10/0275 606/79 |
| 2013/0110145 A1 * | 5/2013 | Weitzman | A61B 17/1642 606/170 |
| 2013/0209980 A1 | 8/2013 | Kuchenbecker et al. | |
| 2013/0218160 A1 * | 8/2013 | Bjorn | A61B 17/1695 606/80 |
| 2013/0296908 A1 * | 11/2013 | Schulte | A61B 17/320068 606/169 |
| 2014/0005681 A1 * | 1/2014 | Gee | A61B 17/320092 606/130 |
| 2014/0012299 A1 * | 1/2014 | Stoddard | A61B 17/320092 606/169 |
| 2015/0088183 A1 * | 3/2015 | Vipperman | A61B 17/1695 606/172 |
| 2015/0182237 A1 * | 7/2015 | Nadzadi | A61B 17/1764 606/80 |
| 2015/0342618 A1 * | 12/2015 | Nguyen | A61B 17/1626 433/27 |
| 2016/0058454 A1 * | 3/2016 | Andersson | A61B 17/1655 600/25 |
| 2016/0066972 A1 * | 3/2016 | Corpa de la Fuente | A61B 17/164 606/92 |
| 2016/0089154 A1 * | 3/2016 | Chien | A61B 17/1626 606/79 |
| 2016/0361070 A1 * | 12/2016 | Ardel | A61B 17/1626 |

* cited by examiner

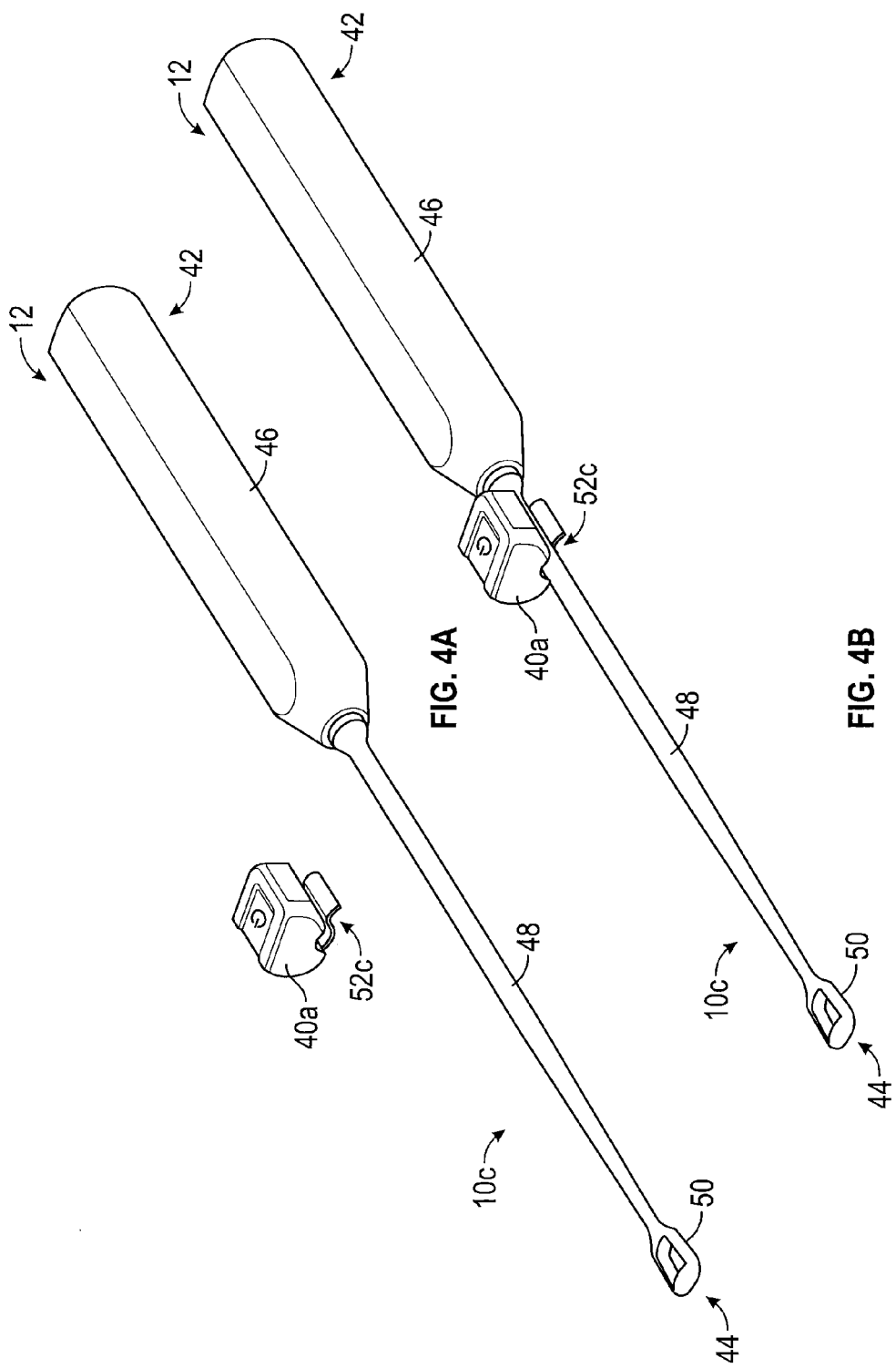

SURGICAL TOOL WITH FEEDBACK

CROSS-REFERENCE TO RELATED APPLICATIONS

Not applicable.

BACKGROUND

Intraoperative physiological monitoring is a continually evolving field that aims to localize, monitor and preserve the structural integrity of structures during surgery or other invasive procedures. In some procedures, tactile and acoustic feedback may be provided by instruments used within spinal fusion procedures to alert surgeons to conditions during a procedure. For example, in some procedures, tactile and acoustic feedback may be acquired using pedicle probes and ball tip feelers. Generally, such feedback may be used to determine, for example, whether or not a process of access has breached the pedicle, or if a pedicle remains intact.

In a spinal fusion procedure, instruments currently provide tactile and acoustic feedback to surgeons by virtue of the interaction between the instrument's distal end and a patient's tissue. Instruments used to remove disc material and cartilage from the interbody space make a unique sound when the distal end of the instrument is scraped against the endplate bone surface. These instruments generally include rasps, rakes, curettes, shavers, Cobb Elevators, Kerrision-Rongeur, ronguer, trials, and the like.

Hearing and feeling these subtle signals made by the distal end of the instruments accurately may take significant training and experience of the surgeon. Acoustic signals provide the added challenge in a noisy operating environment. As such, surgeons have been known to move their head closer to an open wound in order to hear such sounds potentially compromising the surgical environment.

BRIEF DESCRIPTION OF THE SEVERAL VIEWS OF THE DRAWINGS

Like reference numerals in the figures represent and refer to the same or similar element or function. Implementations of the disclosure may be better understood when consideration is given to the following detailed description thereof. Such description makes reference to the annexed pictorial illustrations, schematics, graphs, drawings, and appendices.

FIGS. 4A and 4B illustrate perspective views of another exemplary embodiment of a surgical feedback system in accordance with the present disclosure. The surgical feedback system includes a housing configured to be removably attached to a surgical tool.

DETAILED DESCRIPTION OF INVENTIVE CONCEPT(S)

Figure 1:
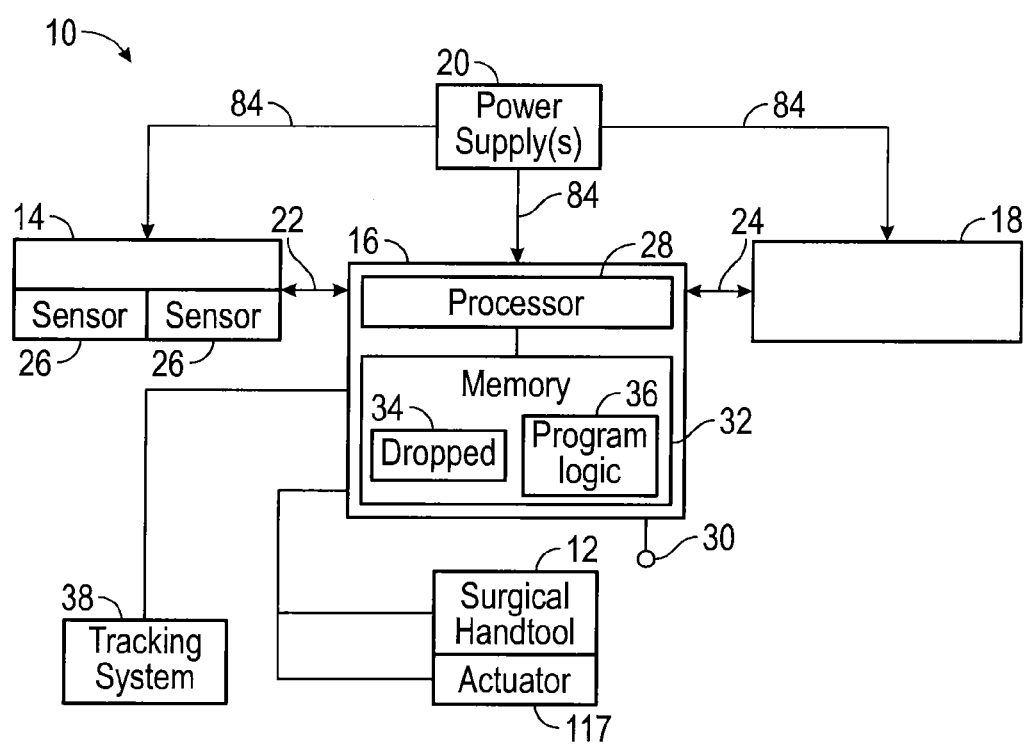
FIG. 1 is a block diagram of a surgical feedback system for intraoperative monitoring within the body throughout at least a portion of a surgical procedure according to the present disclosure.

Before explaining at least one embodiment of the inventive concept(s) disclosed herein in detail, it is to be understood that the presently disclosed and claimed inventive concept(s), process(es), methodology(ies), and/or outcome(s) is not limited in its application to the details of construction and the arrangement of the components or steps or methodologies set forth in the following description or illustrated in the drawings. The presently disclosed and claimed inventive concept(s), process(es), methodology(ies), and/or outcome(s) disclosed herein may be capable of other embodiments or of being practiced or carried out in various ways. Also, it is to be understood that the phraseology and terminology employed herein is for the purpose of description and should not be regarded as limiting the presently disclosed and claimed inventive concept(s), process(es), methodology(ies), and/or outcome(s) herein in any way. With respect to any reference—patent or otherwise—mentioned herein, such reference should be considered to be incorporated by reference herein in its entirety as if set forth explicitly herein.

In the following detailed description of embodiments of the presently disclosed and claimed inventive concept(s), process(es), methodology(ies), and/or outcome(s), numerous specific details are set forth in order to provide a more thorough understanding of the presently disclosed and claimed inventive concept(s), process(es), methodology(ies), and/or outcome(s). However, it will be apparent to one of ordinary skill in the art that the presently disclosed and claimed inventive concept(s), process(es), methodology(ies), and/or outcome(s) within the disclosure may be practiced without one or more of these specific details, by skipping one or more of these specific details, or by modifying or transforming one or more of these specific details in a manner that would be apparent to one of ordinary skill in the art given the present disclosure and teachings. In other instances, well-known features have not been described in detail to avoid unnecessarily complicating the instant disclosure and teachings and the following specification should be construed as including all relevant and/or known details or teachings that would be within the skill and knowledge of one of ordinary skill in the art.

The presently disclosed and claimed inventive concept(s), process(es), methodology(ies), and/or outcome(s) disclosed herein are generally directed to a surgical feedback system for use during a surgical procedure such as, for example, spinal surgery. The surgical feedback system may permit a surgeon to be capable of monitoring auditory signals which may be between 20 Hz to 20 KHz and thereby below an ultrasonic range of frequencies. The auditory signals are generated during surgery, for example, by a cutting edge of a surgical hand tool being used by the surgeon to contact the patient. The presently disclosed and taught surgical feedback system provides the surgeon with electronically amplified and/or transformed acoustic and/or vibration signals for communication of information to the surgeon during surgery to enhance the quality of the surgical procedure. Further, in some embodiments, the acoustic and/or vibration signals may be processed to augment feedback to the surgeon and/or the surgical tool. The surgical feedback system will be described hereinafter in the context of spinal surgery, however, it is to be understood and would be understood by one of ordinary skill in the art given the present disclosure and teachings, that the presently disclosed and claimed inventive concept(s), process(es), methodology(ies), and/or outcome(s) are equally applicable to other types of surgical procedures wherein auditory and/or vibration signals may be used to provide feedback to surgeons and/or surgical tools.

As used herein, the terms "comprises," "comprising," "includes," "including," "has," "having," or any other variation thereof, are intended to cover a non-exclusive inclusion. For example, a process, method, article, or apparatus that comprises a list of elements is not necessarily limited to only those elements, but may include other elements not expressly listed.

As used herein the notation "a-n" appended to a reference numeral is intended as merely convenient shorthand to reference one, or more than one, and up to infinity, of the elements or features identified by the respective reference numeral (e.g., 134a-n). Similarly, a letter following a reference numeral is intended to reference an embodiment of the features of an element that may be similar, but not necessarily identical, to a previously described element or feature bearing the same reference numeral (e.g., 148, 148a, 148b, etc.). Such shorthand notations are used for purposes of clarity and convenience only, and should not be construed to limit the presently disclosed and claimed inventive concept(s), process(es), methodology(ies), and/or outcome(s) in any way, unless expressly stated to the contrary.

Further, unless expressly stated to the contrary, "or" refers to an inclusive "or" and not to an exclusive "or." For example, a condition A or B is satisfied by anyone of the following: A is true (or present) and B is false (or not present), A is false (or not present) and B is true (or present), and both A and B are true (or present).

In addition, use of the term "a" or "an" are employed herein to describe elements and components of the embodiments herein. This is done merely for convenience and to give a general sense of the presently disclosed and claimed inventive concept(s), process(es), methodology(ies), and/or outcome(s). This description should be read to include one or at least one and the singular also includes the plural unless it is readily apparent to one or ordinary skill in the art that it is meant otherwise.

Finally, as used herein, any reference to "one embodiment," "some embodiments," or "an embodiment" means that a particular element, feature, structure, or characteristic described in connection with the embodiments is included in at least one embodiment of the presently disclosed and claimed inventive concept(s), process(es), methodology(ies), and/or outcome(s). The appearance of the phrases "in one embodiment," "in some embodiments," and "in an embodiment" in various places in the specification do not necessarily refer to the same embodiment unless it would be readily apparent to one of ordinary skill in the art that it is meant otherwise.

FIG. 1 illustrates, by way of example only, a block diagram of a surgical feedback system 10 for intraoperative monitoring within the body throughout at least a portion of a surgical procedure according to the present disclosure. In particular, the surgical feedback system 10 may be capable of electronically amplifying and/or transforming acoustic and/or vibration signals being generated through contact between a surgical tool 12 and tissue of a patient to provide feedback to a surgeon and/or the surgical tool 12. In some embodiments, the surgical feedback system 10 may be further capable of processing acoustic and/or vibration signals to augment feedback to the surgeon and/or the surgical tool 12. The acoustic and/or vibration signals may not be reflections of ultrasonic signals that are generated by an ultrasonic transducer. In one embodiment, the acoustic and/or vibration signals have a frequency in a range from 20 Hz to 20,000 Hz.

The surgical feedback system 10 may include one or more input devices 14, one or more control units 16, one or more output devices 18, and one or more power supplies 20, as described in further detail herein. Generally, the input device 14 collects a signal from a surgical environment (optionally converts the signal into another form) and then transmits the signal via a communication link 22 to the control unit 16. The control unit 16 may modify the signal and transmits the signal via a communication link 24 to the output device 18. The output device 18 may provide the signal to an audience of only one person (e.g., headphones), an audience of more than one person (e.g., speakers), or both. For example, the output device 18 may provide the signal to a surgeon or an operating environment (e.g., entire operating room) in a mode easily comprehended by a surgeon or staff. Each of the input device 14, control unit 16 and output device 18 may have individual power supplies 20, or at least one of the input device 14, control unit 16 and output device 18 may share a power supply 20.

In some embodiments, the input device(s) 14, the control unit(s) 16, the power supply(ies) 20 and/or the output device(s) 18 may be housed in a single device or may be housed in separate devices. For example, in some embodiments, the input device 14, such as a microphone, may be positioned on or near the surgical tool 12 near the surgical site in order to transduce auditory signals. The control unit 16, such as a processor, and/or output device 18, such as speakers, may be located remotely from the microphone with each of the microphone, processor and/or speakers having separate power supplies 20, for example. The microphone may convert auditory signals in the form of vibrations and/or pressure into a form that is understandable by the control unit 16, such as analog electrical signals. In this instance, the control unit 16 may include an analog to digital converter (or other suitable component) to receive the analog electrical signals and convert the analog electrical signals into digital information that can be interpreted and/or processed by the control unit 16. The control unit 16 may be constructed entirely of analog components with or without processing capabilities, digital components with or without processing capabilities or a combination of analog and digital components with or without processing capabilities.

In some embodiments, the input device(s) 14, control unit(s) 16, and/or output device(s) 18 may be modular and attach to various surgical tools 12 (e.g., surgical tools include but are not limited to surgical hand tools having a cutting edge such as a rasp, a curette or the like). For example, the input device(s) 14 may be mounted on a surgical tool 12 to provide for adequate acquisition of an acoustic or vibration signal. The control unit 16 and output device 18, however, may be mounted for ergonomics, for example. As such, the input device 14, control unit 16 and output device 18 may attach to various surgical tools 12 as desired. Even further, the control unit 16 may be entirely separate from the input device 14, for example, with the input device 14 positioned near the surgical site for interaction with the surgical environment to acquire the acoustic and/or vibration signal. In this example, the control unit 16 may be located remotely with output incorporated into surgical interfaces including, but not limited to, intraoperative C-Arm, Image Guided Surgery system, surgical microscopes, video monitors, and/or the like.

The one or more input devices 14 may include one or more sensors 26. Generally, the one or more sensors 26 may be configured to generate signals (e.g., acoustic and/or vibration signals) from a surgical environment (e.g., surgical target site on vertebra). For example, the one or more sensors 26 may be configured to collect at least one of an acoustic signal or a vibration signal generated by the surgical tool 12. Generally, the one or more sensors 26 may be capable of converting sound waves and/or vibrations into electrical energy to be amplified, transmitted, stored, and/or recorded.

In some embodiments, the one or more sensors 26 may include an audio system consisting of one or more microphones and/or the like. For example, one or more microphones may be an acoustic-to-electric transducer capable of converting sound passing through air and/or solid objects in a surrounding environment into an electrical signal.

In some embodiments, the one or more sensors 26 may include a contact microphone which is otherwise known as a pickup or a piezo. A contact microphone is a form of microphone designed to sense audio vibrations through solid objects. Unlike normal air microphones, contact microphones are almost completely insensitive to air vibrations but transduce only structure-borne sound which makes the contact microphone insensitive to interference caused by ambient noise within the operating room.

In some embodiments, the one or more sensors 26 may use piezoelectricity to produce an electrical signal from audio vibrations. In other examples, the one or more sensors 26 may use electromagnetic induction, capacitance changes, and/or the like.

In some embodiments, one or more sensors 26 may detect vibration signals. For example, at least one sensor 26 may use one or more accelerometers, one or more velocity sensors, one or more proximity sensors, and/or the like to collect vibration signals indicative of audio vibrations within the surgical environment.

In some embodiments, the one or more sensors 26 may include a wireless sensor (e.g., wireless microphone). For example, at least one sensor 26 may include a radio transmitter such that the sensor may transmit one or more signals to cell phones, wireless computer networks, Bluetooth enabled devices, radios, and/or any other devices capable of receiving signals from the sensor 26 for use as described herein.

Location of the one or more sensors 26 during a surgical procedure may be determined to provide adequate acquisition of the acoustic and/or vibration signal. Further, in some embodiments, after positioning of the one or more sensors 26, each sensor 26 may be tuned to eliminate known acoustic and/or vibration noise within the surgical area and/or operating environment, such as operating room background noises, monitors beeping, typical operating room staff movements/shuffles, equipment being moved, sounds produced by respiration equipment, in-situ noise including banging or scraping the surgical tool 12 against another device or other instruments.

The input device 14 and the control unit 16 may be provided as a single device or located remotely from one another. For example, in some embodiments, the one or more sensors 26 may receive acoustic signals and provide the signals via wires or by wireless communication to the control unit 16. Alternatively, the control unit 16 may be remotely located, such as, in the operating room environment, for example, and the signals may be provided via wires or wireless to the control unit 16. For example, at least one sensor 26 may comprise a first wireless transceiver, and the control unit 16 may comprise a second wireless transceiver configured to communication with the first wireless transceiver. In some embodiments, the first and second wireless transceivers may be further configured to communicate with a network protocol.

The control unit 16 may include one or more processors 28. The one or more processors 28 may be capable of interfacing and/or communicating with the input device 14 via communication link 22 and the output device 18 via communication link 24. For example, the one or more processors 28 may by capable of communicating via the communication links 22 and 24 by exchanging signals (e.g., analog, digital, optical, and/or the like). The communication links 22 and 24 may be wired communication links, wireless communication links, or a combination thereof.

The communication links 22 and 24 may interface with the one or more processors 28 and the input device 14 and/or output device 18 in a variety of ways. For example, the communication links 22 and 24 may interface by optical and/or electronic interfaces, and/or may use a plurality of network topographies and/or protocols including, but not limited to, Bluetooth, Wi-Fi, biotelemetry, infrared (IR), ultrasound, Ethernet, TCP/IP, circuit switched paths, combinations thereof, and/or the like. For example, in some embodiments, the communication links 22 and 24 may be implemented as the World Wide Web (or Internet), a local area network (LAN), a wide area network (WAN), a wireless local area network (WLAN), a metropolitan network, a wireless network, a cellular network, a GSM-network, a CDMA network, a 3G network, a 4G network, a satellite network, a radio network, an optical network, a cable network, a public switch telephone network, an Ethernet network, combinations thereof, and/or the like. Additionally, the communication links 22 and 24 may use a variety of protocols to permit uni-directional or bi-directional interface and/or communication of data and/or information between the one or more processors 28 and the input device 14 and/or output device 18.

In some embodiments, the one or more processors 28 may use a network protocol to communicate via communication links 22 and 24, for example. To that end, in some embodiments, each element of the control unit 16 may be partially or completely net-worked based or cloud-based, and may not be located in a single physical location. The network may permit uni-directional or bi-directional communication information and/or data between the one or more processors 28, the input device 14 and/or the output device 18. For example, in some embodiments, the communication link 22 may provide communication between the control unit 16 and the one or more sensors 26 permitting bi-directional communication of information and data. As used herein, the terms "network-based," "cloud-based", and any variation thereof, are intended to include the provision of configurable computational resources on demand via interfacing with a computer and/or a computer network, with software and/or data at least partially located on the computer and/or computer network.

The one or more processors 28 may be implemented as a single processor or multiple processors working together, or independently, to execute the logic as described herein. Each processor 28 may be capable of reading and/or executing processor executable code and/or capable of creating, manipulating, retrieving, altering and/or storing data structure.

Exemplary embodiments of the one or more processors 28 may include, but are not limited to, a digital signal processor (DSP), a central processing unit (CPU), a field programmable data array (FPGA), a microprocessor, a multi-core processor, combinations thereof, and/or the like, for example. In some embodiments, additional processors 28 may include, but are not limited to implementation as a personal computer, a cellular telephone, a smart phone, a network-capable television set, a television set-top box, a tablet, an e-book reader, a laptop computer, a desktop computer, a network-capable handheld device, a server, a digital video recorder, a DVD-player, a Blu-Ray player, and/or combinations thereof, for example.

The one or more sensors 26 may be capable of receiving acoustic and/or vibration signals and may be capable of transmitting such signals to the one or more processors 28. In some embodiments, the one or more processors 28 may be capable of receiving additional information via a user and/or processors via one or more input units 30. For example, during a surgical procedure, the surgeon may supply additional information via voice command to the one or more processors 28. The one or more input units 30 may include, but are not limited to, implementation as a keyboard, touchscreen, mouse, trackball, microphone, fingerprint reader, infrared port, slide-out keyboard, flip-out keyboard, cell phone PDA, cell phone, a fax machine, a printer, a laptop computer, combinations thereof, and/or the like, for example. It is to be understood that in some exemplary embodiments, the one or more input units 30 may be implemented as a single device, such as, for example, a touchscreen or a tablet. It is to be further understood that as used herein the term "user" is not limited to a human being, or the surgeon, and may comprise, a computer, a server, a website, a processor, a network interface, a human, a user terminal, a virtual computer, combinations thereof, and/or the like, for example.

The one or more processors 28 may be capable of communicating with one or more memories 32 via a path (e.g., data bus). The one or more memories 32 may be capable of storing processor executable code. Additionally, the one or more memories 32 may be implemented as a conventional non-transient memory, such as, for example, random access memory (RAM), a CD-ROM, a hard drive, a solid state drive, a flash drive, a memory card, a DVD-RIM, a floppy disk, an optical drive, combinations thereof, and/or the like.

In some embodiments, one or more memories 32 may be located in the same physical location as the processor 28, and/or one or more memories 32 may be located remotely from the processor 28. For example, one or more memories 32 may be located remotely from the processor 28 and communicate with other processors 28 via the network. Additionally, when more than one memory 32 is used, a first memory may be located in the same physical location as the processor 28 and additional memories 32 may be located in a remote physical location from the processor 28. Additionally, one or more memories 32 may be implemented as a "cloud memory" (i.e., one or more memories 32 may be partially or completely based on or accessed using the network).

The one or more memories 32 may store processor executable code and/or information comprising one or more databases 34 and program logic 36. In some embodiments, the processor executable code may be stored as a data structure, such as a database and/or data table, for example. In some embodiments, signals acquired by the sensors 26 may be stored in one or more databases and/or data tables 34 within the one or more memories 32.

The one or more processors 28 may be used to provide modification of the original signal acquired by the input device 14. Modification of the original signal may include amplification, frequency shifting, filtering, codification, conversion, interpretation and/or the like, for example, as described in further detail herein.

In some embodiments, the original signal acquired by the sensor 26 of the input device 14 may be amplified by the control unit 16, and the modified signal transmitted to the output device 18. For example, in some embodiments, an original acoustic signal acquired by the sensor 26 may be amplified and provided to the output device 18. Amplification of the original acoustic signal may aid a surgeon in recognition of a particular sound for a procedure. For example, during spinal fusion surgery, endplates of vertebral bodies may be prepared to expose bleeding bone. Surgical tools 12 removing disc material and cartilage from interbody space provide a unique sound when scraped against endplate bone surfaces. The input device 14 may acquire an original acoustic signal at the surgical site of the unique scraping sound, and transmit the original acoustic signal to the control unit 16 via the communication link 22. The control unit 16 may amplify the scraping sound (i.e., original acoustic signal), and transmit the amplified scraping sound (i.e., modified acoustic signal) to the output device 18 via the communication link 24. Amplification of the scraping sounds may provide a sound that is comprehensible for the surgeon and staff and aid the surgeon in recognizing what material the surgical tool 12 is removing during the procedure.

In some embodiments, the original signal (e.g., acoustic and/or vibration) acquired by the sensor 26 may be filtered by the control unit 16. The control unit 16 may then transmit the modified signal to the output device 18. For example, the original signal may be filtered to accentuate a desired frequency, reduce sampling frequency, prevent signal aliasing, and/or the like.

Figure 11:
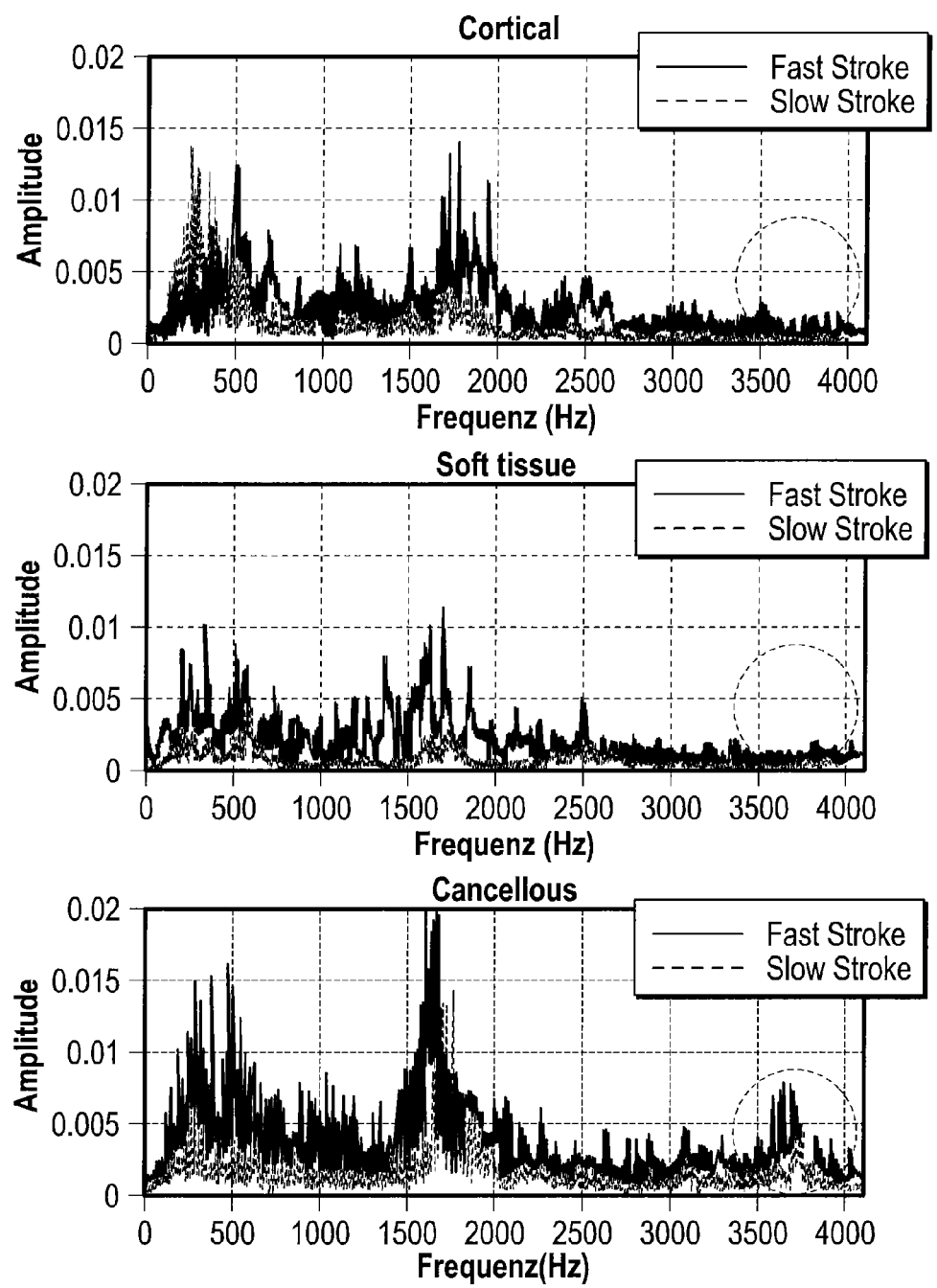
FIG. 11 is a graph showing frequency domain signals collected by the surgical feedback system and showing different frequency spectra produced by a cutting edge of a surgical tool contacting cortical tissue, soft tissue and cancellous tissue.
Figure 12:
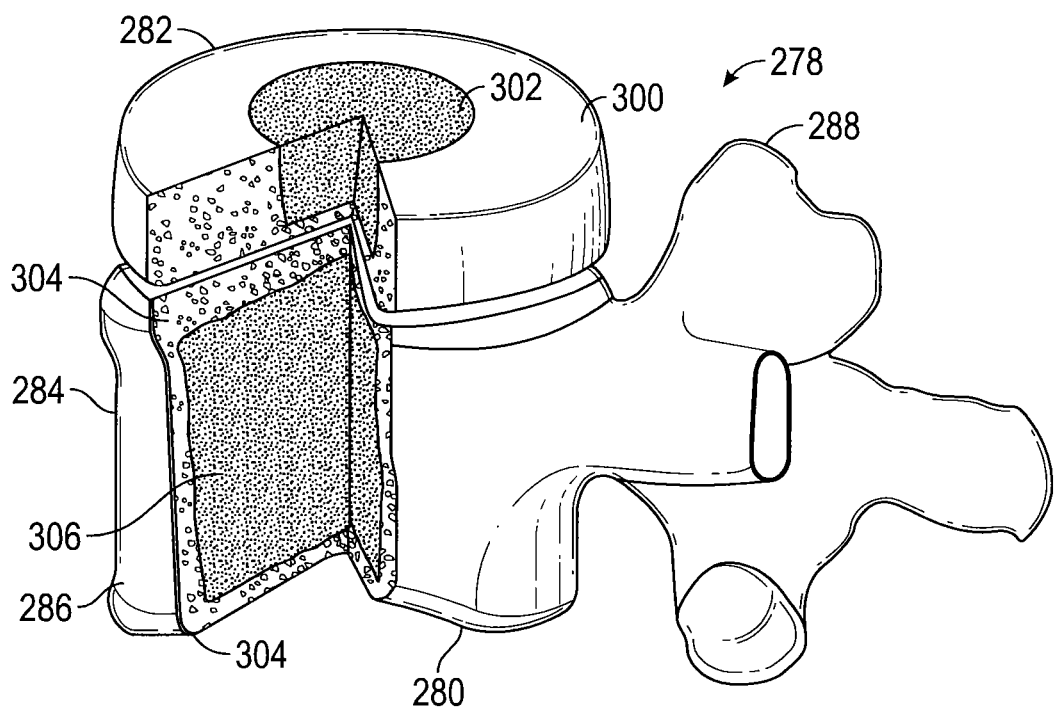
FIG. 12 is a partial, perspective view of a section of a spinal column including a vertebrae and an intervertebral disc.

Referring to FIGS. 1, 11 and 12, in some embodiments discussed below, the original signal acquired by the sensor 26, which may be in the time domain, may be converted into a frequency domain and then interpreted by the control unit 16. A time-domain graph of the original signal shows how the signal changes over time, whereas a frequency-domain graph shows how much of the signal lies within each given frequency band over a range of frequencies. By analyzing the level of the original signal within one or more frequency ranges, the control unit 16 can discriminate between the types of tissues that are being contacted by the surgical tool 12. For example, to determine when the surgical tool 12 is contacting cancellous tissue shown in FIG. 12, the control unit 16 may convert the original signal into the frequency domain and then monitor the frequency range between 3500 Hz and 4000 Hz. FIG. 11 illustrates three graphs showing frequency domain signals of audio signals (e.g., different frequency spectra) collected by the sensor 26 of the surgical feedback system 10. In each of these examples, the audio signals were produced by a cutting edge of the surgical tool 12 contacting tissue. More specifically, in FIG. 11, the audio signals were produced by the cutting edge of the surgical tool 12 separately contacting bovine cortical tissue, soft tissue and cancellous tissue. When a level of the original signal within the frequency range between 3500 Hz and 4000 Hz exceeds a predetermined baseline for a predetermined period of time, for example, the control unit 16 may conclude that the surgical tool 12 is contacting cancellous tissue, rather than cortical tissue or soft tissue. This conclusion can be used for a variety of purposes. For example, the control unit 16 can generate an alert to notify the surgeon of the type of tissue being contacted. In this instance, the alert can be provided in any manner that is capable of being perceived by the surgeon, such as by providing an electrical signal to the output device 18 to cause the output device 18 to generate a visual alert, audio alert and/or a tactile (e.g., vibratory) alert. Or, the control unit 16 can generate instructions to modify the operation of the surgical tool 12 as discussed in detail below. Thus, a surgeon may be alerted, for example, that a cutting tool on a surgical tool 12 has reached a particular tissue, or bone by a vibration signal corresponding to a pre-determined frequency or intensity of the original audio signal(s). To that end, the control unit 16 may direct the surgical tool 12 to vibrate.

The original signal can be converted from the time domain to the frequency domain by any suitable conversion algorithm, such as a Fourier series, a Fourier transform, a Laplace transform, or a Z transform. Each of these transforms are known in the art (for purposes other than to discriminate between different types of tissue being contacted by the surgical tool 12). Thus a detailed explanation of how to make and use such transforms is not believed to be necessary to enable one skilled in the art to make and use the presently disclosed and claimed inventive concepts.

In another example of signal conversion, the original signal(s) (e.g., acoustic or vibration) received by the input device 14 via the one or more sensors 26 may be converted by the control unit 16 to one or more visual signals. For example, one or more acoustic signals may be converted to one or more visual signals correlating to a mechanical and/or electronic display for transmission by the output device 18. The converted visual signal (i.e., modified signal) may correlate to the original acoustic signal(s) frequency and/or intensity. For example, a surgeon may be alerted that a cutting tool on a surgical tool 12 has reached a particular tissue, or bone by a visual signal corresponding to a pre-determined frequency or intensity of the original audio signal(s).

In yet another example of signal conversion, the original signal(s) (e.g., acoustic or vibration) received by the input device 14 via the one or more sensors 26 may be converted by the control unit 16 to one or more visual signals, with each visual signal having a brightness component. The brightness component may provide a visual correlation to the frequency and/or intensity of the original signal(s) received by the input device 14. For example, differences in luminance on a visual display of the output device 18 may be correlated with the presence of a frequency within a predetermined frequency range and/or intensity of the original signal within the predetermined frequency range of the original signal(s) received by the input device 14.

In another example of signal conversion, the original signal(s) (e.g., acoustic or vibration) received by the input device 14 via the one or more sensors 26 may be converted by the control unit 16 to one or more visual signals, with each visual signal having a color output. The color output of each visual signal may provide a visual correlation to the frequency and/or intensity of the original signal(s) received by the input device 14. For example, differences in color on a visual display of the output device 18 may be correlated with the presence of a frequency within a predetermined frequency range and/or intensity of the original signal within the predetermined frequency range received by the input device 14.

In some embodiments, the original signal(s) (e.g., vibration or acoustic) acquired by the sensor 26 may be analyzed by the control unit 16 to assist in providing information to the surgeon regarding the type of tissue that the surgical tool 12 is contacting. Shown in FIG. 12 is a section of a spinal column 278 including a vertebrae 280 and an intervertebral disc 282. The vertebrae 280 has a body 284, which includes an anterior middle portion 286 called the centrum and a posterior vertebral arch 288, also called a neural arch. The intervertebral disc 282 is provided with an annulus fibrosus 300 and a nucleus pulposus 302. The body 284 is composed of one or more cortical endplate 304, and cancellous vertebral body bone 306. The annulus fibrosus 300 and the nucleus pulposus 302 extend across and are in contact with the cortical endplate 304. The cortical endplates 304 of the body 284 of the vertebrae 280 are flattened and rough in order to give attachment to the intervertebral discs 282. The cortical endplates 304 are in direct contact with the intervertebral discs 282 and form the joint. The endplates 304 are formed from a thickened layer of the cancellous bone of the vertebral body, the top layer being more dense. The cortical endplates 304 function to contain the adjacent discs, to evenly spread the applied loads, and to provide anchorage for the collagen fibres of the disc. They also act as a semi-permeable interface for the exchange of water and solutes.

As a surgeon is using a cutting tool on the surgical tool 12 to remove one of the intervertebral discs 282 and prepare the cortical endplates 304 for a replacement intervertebral disc, the control unit 16 can receive signals from the sensor 26 and output signals indicative of the types of tissues that the cutting tool is contacting. For example, the frequency of the original signal can be shifted by the control unit 16. For example, in some embodiments, at least two or more pure tone outputs of the original acoustic signal acquired by the sensor 26 may be used to represent ranges of frequency from the original signal. The two or more pure (or mixed) tone outputs can each represent a particular tissue type, for instance annulus fibrosus 300, nucleus pulposus 302, cortical endplate 304, and cancellous vertebral body bone 306 as illustrated in FIG. 12, for example. The two or more pure or mixed tone outputs may also represent a surface characteristic, roughness, hardness or substrate indication/identification. In another example, lower frequency signals may be difficult to hear by a surgeon within an operating environment (e.g., operating room). As such, lower frequency signals collected by the input device 14 may be transmitted to the control unit 16. The control unit 16 may shift the lower frequency signals to a higher frequency in order to enhance the audibility of the lower frequency signals to the surgeon. As such, the band of frequencies being generated may be compressed to a band optimized for human hearing (e.g., 2 kHz-5 kHz), for example.

In some embodiments discussed above, frequency analysis may be performed by the control unit 16 on the original signal (e.g., acoustic or vibration) acquired by the sensor 26. For example, in some embodiments, the original signal acquired by the sensor 26 may be analyzed using analysis techniques including, but not limited to, Discrete Fourier Transform, Discrete Time Fourier Transform (e.g., Fast Fourier Transform), Laplace Transform, Z Transform, Hillbert Transform, Discrete Cosine Transform (e.g., single, multidimensional) I-VIII, and/or the like. Using a frequency analysis, the original signal in the time domain may be converted into the frequency domain and analyzed by the control unit 16 to determine the presence and/or the absence of particular tissue being contacted by the surgical tool 12. The original signal in the frequency domain can be displayed by the output device 18 in a graphic format. For example, the original signal may be displayed to show frequency over time as a result of one or more of the frequency analysis techniques. The data may then be presented as a line of color over time. The line of color may include a plurality of colors mapped to frequency and brightness of colors mapped to intensity of frequency over time, for example.

Further, modification of the original signal by the control unit 16 may incorporate analysis techniques to identify and/or compare features such as the presence of the original signal in the 3500-4000 frequency range. As discussed above, the presence of the original signal in the 3500-4000 frequency range above a predetermined baseline in the frequency domain indicates that the surgical tool 12 is contacting cancellous material. Such techniques may include, but are not limited to, Singular Value Decomposition (Principal Component Analysis and/or other orthogonal transforms), multilinear PCA, factor analysis, multiple factor analysis, co-inertia analysis, STATIS, DISTATIS, Correspondence Analysis, canonical correlation analysis, K-means clustering, multilinear subspace learning, correlated clustering, Tucker decomposition, linear discriminant analysis, nonlinear dimensionality reduction, and/or the like.

In some embodiments, the control unit 16 may process the original signal (e.g., acoustic and/or vibration), and determine one or more tissue type or surface type associated with original signal. For example, the original signal may be compared with a library including records (e.g., each record denoting a particular tissue type or surface type) of template signals stored within the database 34 (e.g., tissue or surface database) to determine the likelihood the original signal represents the instrument interacting with a specific tissue type or surface type. The analysis may utilize feature detection, audio fingerprinting techniques, and/or other data similarity algorithms. Exemplary surface types include, but are not limited to, surface characteristic, roughness, hardness or substrate indication/identification.

To build the library of samples that correlate with specific tissue or surface types, audio data is collected by one of the sensors 26 (e.g., a microphone) of the surgical tool 12 contacting a particular type of tissue or surface type at a particular combination of selected from the group consisting of, but not limited to, tool speed, contact angle, and pressure, for example. This process is repeated to create datasets for a variety of different combinations factors, including but not limited to tissue, tool speed and pressure. The exemplary factors discussed herein including, but not limited to the tool speed, pressure and type of tissue are independent variables.

Then, unique features for each tissue or surface are identified (e.g. energy at a specific frequency or group of frequencies) that are present at all tool speeds and pressures. Once the unique features for each tissue or surface are identified, the records within the library are created with each record having a field with data identifying a particular tissue or surface type and other fields having the unique features for each tissue or surface type. The database is used by collecting the original signal discussed above, which in some embodiments is an analog signal in the time domain. Then, the analog signal is digitized and converted into the frequency domain by way of a Fast Fourier transform, for example. Then, data indicative of the frequency domain of original signal is correlated with features in the library to identify a best fit match. For example, the feature might be a combination such as: a significant peak of energy from 1000-1300 Hz in the range from 500-2000 Hz and a significant peak of energy from 3250-3500 Hz in the range from 2500-4000 Hz to identify that the surgical tool is contacting cancellous tissue. If the best fit match is of or exceeds a specified threshold, then the control unit 16 generates a signal that indicates the type of tissue or surface correlated with the sample and transmits the signal to the output device 18. The output device 18 receives the signal and then communicates the type of tissue or surface to the surgeon through any suitable methodology, such as by display the type of tissue or surface through light, analog meter, or sound feedback.

In some embodiments, the original signal(s) may include acoustic signals having pure or mixed tones that correlate with tissue type or surface type on a scale related to a surgical procedural step. The control unit 16 may convert the tones to audio or visual representation of the tissue type or surface type based on the data stored in the database 34 (e.g., tissue or surface database), and transmit the data to the output device 18 for transmission to the surgeon, for example.

In some embodiments, the original signal collected by the input device 14 and/or the modified signal provided by the control unit 16 may be transmitted, recorded, and/or processed to create processed data. Processing may occur before or after transmission of the original signal and/or the modified signal to the output device 18. In some embodiments, the original signal, modified signal, and/or processed data may be stored with one or more additional patient data, such as blood loss, surgery duration, time to clear a targeted tissue for removal, surgery outcome records and/or the like. Stored data may be used to determine best practice techniques for a particular surgical procedure.

In some embodiments, the control unit 16 may analyze the original signal, and using the analysis, control one or more functions of a surgical tool 12. For example, the control unit 16 may analyze the original signal, and use the analysis in a feedback loop to control the surgical tool 12, such as, for example, activating and/or deactivating an actuator to effect the ability of the surgical tool 12 to operate on the patient's tissue.

In some embodiments, the control unit 16 may use the analyzed signal to activate or deactivate the ability of the surgical tool 12 to cut tissue. Generally, if the analyzed signal indicates that tissue being confronted by the surgical tool 12 is to be left intact, the control unit 16 may communicate a signal to the surgical tool 12 to deactivate the ability of the surgical tool 12 to cut. In another example, the control unit 16 may use the analyzed signal to activate or deactivate force of the surgical tool 12 (e.g., applied force by the surgeon). For example, if the analyzed signal indicates that tissue being confronted by the surgical tool 12 is to be left intact, the control unit 16 may communicate a signal to the surgical tool 12 to deactivate transmission of the force applied by the surgeon to a cutting surface of the surgical tool 12 to modulate and/or reduce the ability of the surgical tool 12 to cut tissue.

The modified signal may be provided by the control unit 16 to the one or more output devices 18. It should be noted that in some embodiments, the surgical feedback system 10 may be configured such that data from the input device 14 may integrate directly to the output device 18 without the use of the control unit 16.

In some embodiments, the control unit 16 and the output device 18 may be implemented as a single device, such as, for example, a speaker system. Additionally, in some embodiments, the input device 14, the control unit 16 and the output device 18 may be implemented as a single device having a common housing.

The output device 18 may be capable of outputting information in a form perceivable by a user and/or processor(s). For example, transmittal of information may use methods including, but not limited to, computer speech, tones and volume, color and/or brightness indications, text display, graphic display, audio sounds, vibration signals, and/or the like.

The one or more output devices 18 may be mounted on the surgical tool 12 or positioned external to the surgical environment, positioned within the operating environment, positioned outside the operating environment, and/or the like. For example, in some embodiments, the output device 18 may be displayed on an independent display such as a flat panel or heads up display.

The one or more output devices 18 may include, but are not limited to, implementation as a speaker, a monitor, a screen, a touchscreen, television set, a smart phone, a PDA, a cell phone, a fax machine, a printer, a laptop computer, combinations thereof, and/or the like, for example. For example, in some embodiments, the one or more output devices 18 may include one or more speakers transmitting the modified signals from the control unit 16 to a user and/or processor. To that end, an acoustic signal collected by a microphone (input device 14) may be modified (e.g., amplified) and transmitted by one or more speakers (output device 18) within the operating environment (e.g., operating room). It is to be understood that as used herein the term "user" is not limited to a human being, and may comprise, a computer, a server, a website, a processor, a network interface, a human, a user terminal, a virtual computer, combinations thereof, and/or the like, for example.

In some embodiments, the surgical feedback system 10 may optionally include a tracking system 38 with the tracking system 38 using surgical navigation techniques. The tracking system 38 may be used in conjunction with the input device 14 to identify the location of the surgical tool 12. By using the location of the surgical tool 12, a two and/or three dimensional spatial map of the surgical area may be formed. In one example, contours of an endplate and osteophytes may be visualized using the two and/or three dimensional map. The spatial map may be displayed using the output device 18. For example, the output device 18 may be a two or three dimensional graphic display located on the surgical tool 12 and/or a separate graphic display system (e.g., flat panel, head up display).

Figure 2A:
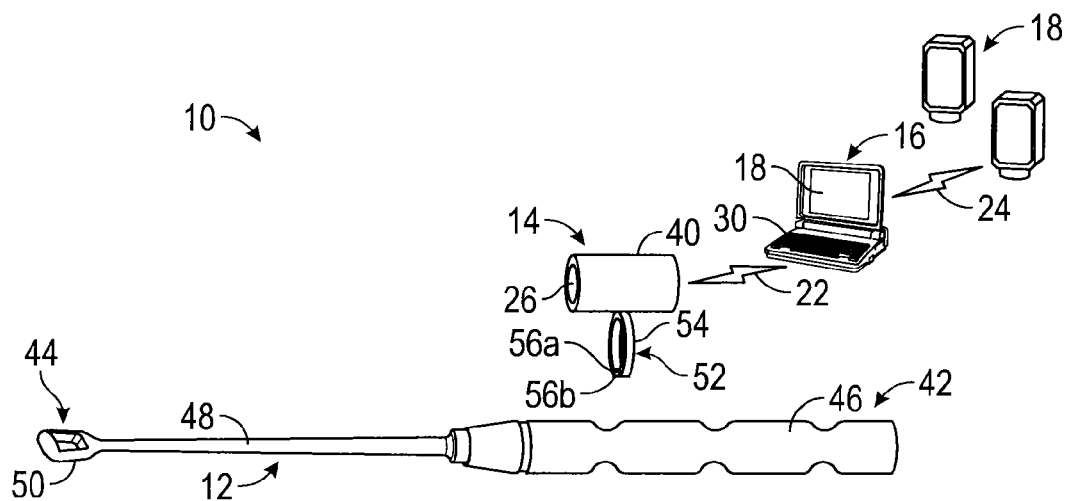
FIGS. 2A and 2B illustrate schematic views of an exemplary embodiment of a surgical feedback system in accordance with the present disclosure. A housing of the surgical feedback system is removably attached to a surgical tool.

FIG. 2A illustrates an exemplary embodiment of a surgical feedback system 10 having one or more sensors 26 supported or encompassed within a housing 40. The housing 40 may be permanently or removably attached to a surgical tool 12. FIG. 2A illustrates an exemplary embodiment wherein the housing 40 is removably attached to the surgical tool 12.

The housing 40 may support or encompass the one or more sensors 26. Dimensions, including size and shape of the housing 40, may be determined based on the size and shape of the sensors 26.

The surgical tool 12 may generally include a proximal end 42 and a distal end 44. It should be noted that the surgical tool 12 illustrated in FIG. 2 is an exemplary hand tool, and one skilled in art will appreciate that the housing 40 of the input device 14 may be permanently or removably attached to any surgical tool 12 having a connectable portion, such as a shaft and/or handle as described in further detail herein.

The proximal end 42 of the surgical tool 12 may include a handle 46 configured for use and manipulation by a surgeon. The handle 46 may be connected by a shaft 48 to a functional tool 50 (e.g., cutting tool). The functional tool 50 may be positioned on the distal end 44 of the surgical tool 12.

The housing 40 may include a fastener 52. The fastener 52 may be configured for attachment to a connectable portion of the surgical tool 12. For example, the fastener 52 may be configured for attachment to the handle 46 and/or the shaft 48.

Figure 4C:
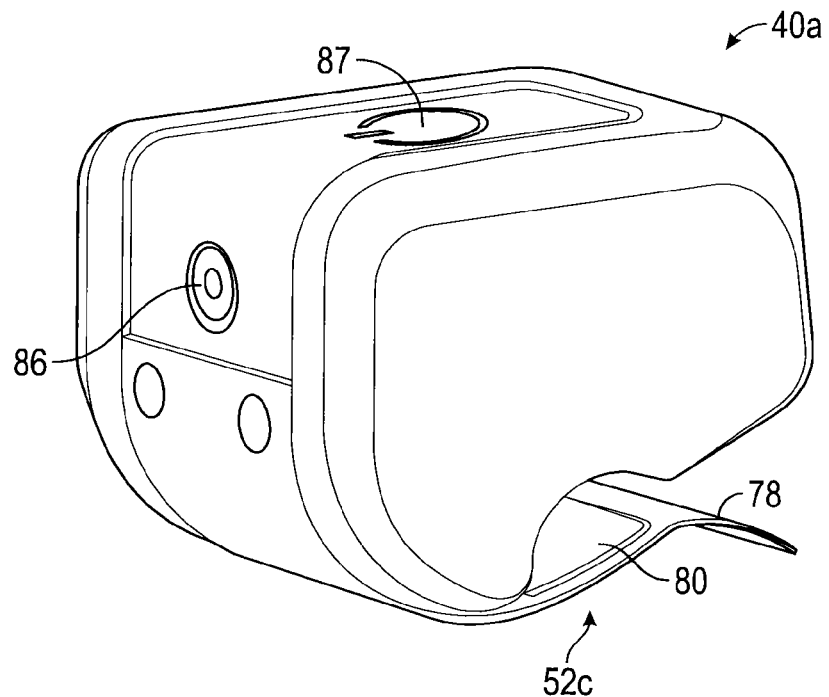
FIGS. 4C and 4D illustrate perspective views of an exemplary housing for use in the surgical feedback system illustrated in FIGS. 4A and 4B.

FIG. 2A also illustrates an exemplary embodiment of the fastener 52. The fastener 52 includes a C-shaped ring 54 having a plurality of ends 56a and 56b. The ends 56a and 56b may be positioned a set distance apart from one another such that the ends 56a and 56b may be wedged (or otherwise moved) further apart for placement about the handle 46 or shaft 48 of the surgical tool 12. In one embodiment, the fastener 52 may be spring clip 78 as shown in FIG. 4C.

Figure 2B:
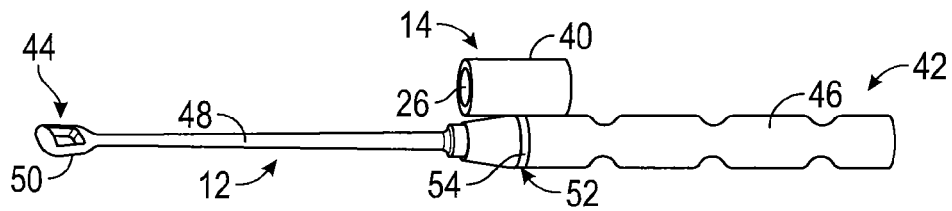

FIG. 2B illustrates the fastener 52 of FIG. 2A positioned about the handle 46 of the surgical tool 12. In some embodiments, the ring 54 may be formed of semi-flexible material (e.g., plastic) such that the ends 56a and 56b, once positioned about the handle 46 or shaft 48 of the surgical tool 12, may return to an original resting state. For example, the ends 56a and 56b may initially be at a first resting position and wedged apart to a second position for removable attachment about the handle 46 of the surgical tool 12. Once positioned in place about the handle 46, the ends 56a and 56b may return to the first resting position.

Figure 2C:
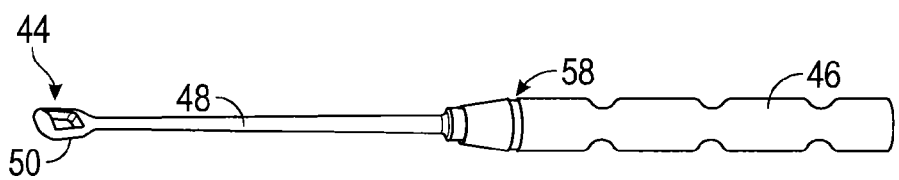
FIG. 2C illustrates a side view of an exemplary surgical tool for use with the surgical feedback system of FIGS. 2A and 2B. The surgical tool has at least one groove.

FIG. 2C illustrates an exemplary surgical tool 12 having one or more grooves 58. Grooves 58 may be positioned in the handle 46 and/or the shaft 48 of the surgical tool 12. For example, FIG. 2C illustrates the surgical tool 12 having the groove 58 positioned in the handle 46 of the surgical tool 12. The groove 58 may aid in positioning of the fastener 52 during use of the surgical tool 12. Dimensions of the groove 58 may be determined based on width of the ring 54 and/or size of one or more ends 56a or 56b. The ends 56a and 56b may grip the groove 58 such that the fastener 52 is removably attached to the surgical tool 12. The groove 58 The groove 58 may be fully circumferential or partially circumferential. It should be understood that the groove 58 is representative of a plurality of possible mating features. The handle 46 and/or the shaft 48 may have other configurations that facilitate the positioning and/or connection of the handle 46 and/or the shaft 48 with the fastener 52. For example, the handle 46 and/or the shaft 48 may include one or more proud features rather than a relief feature; a flat feature or a dimple; a ball groove or a rectangular groove or a "v" notch or a hole.

Referring to FIGS. 1 and 2A, in some embodiments, the housing 40 may also encompass and/or also support the control unit 16 or a portion of the control unit 16. It is to be understood, that in certain embodiments, the one or more processors 28 may be located within the housing 40 and attached (i.e., temporarily or permanently) to the surgical tool 12 during use within the surgical environment. In some embodiments, portions of the control unit 16 may be positioned within the housing 40 or on the surgical tool 12, with additional portions of the control unit 16 located remotely from the surgical tool 12 (e.g., within the operating room). For example, one or more first processors 28 may be positioned within the housing 40 and/or on the surgical tool 12, with one or more second processors 28 located remotely from the surgical tool 12 within the operating environment (e.g., operating room).

Figure 2D:
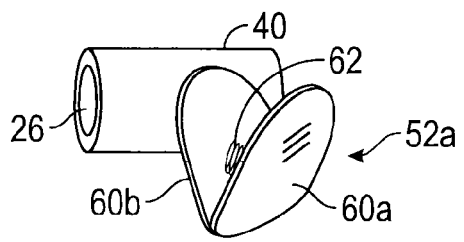
FIG. 2D illustrates an exemplary fastener for use in the surgical feedback system illustrated in FIGS. 2A and 2B. The fastener includes a plurality of legs connected by a spring for temporary attachment to a surgical tool.

FIG. 2D illustrates another exemplary embodiment of a fastener 52a for use with the housing 40 of FIG. 2A. The fastener 52a maybe in the form of a spring clip comprising a plurality of legs 60a and 60b forced together by a spring 61. The legs 60a and 60b may be coated with a non-skid material to assist the legs 60a and 60b to grip the surgical tool 12 during use. As the legs 60a and 60b may be spring loaded and adjustable, the fastener 52a may be adjusted during use of the surgical tool 12 and moved to and from different elements (e.g., handle 46, shaft 48) having different widths along the surgical tool 12. For example, in a first position, the fastener 52a may be removably attached to the handle 46 of the surgical tool 12, and subsequently moved to a second position at the shaft 48 of the surgical tool 12 during a surgical procedure.

Figure 3A:
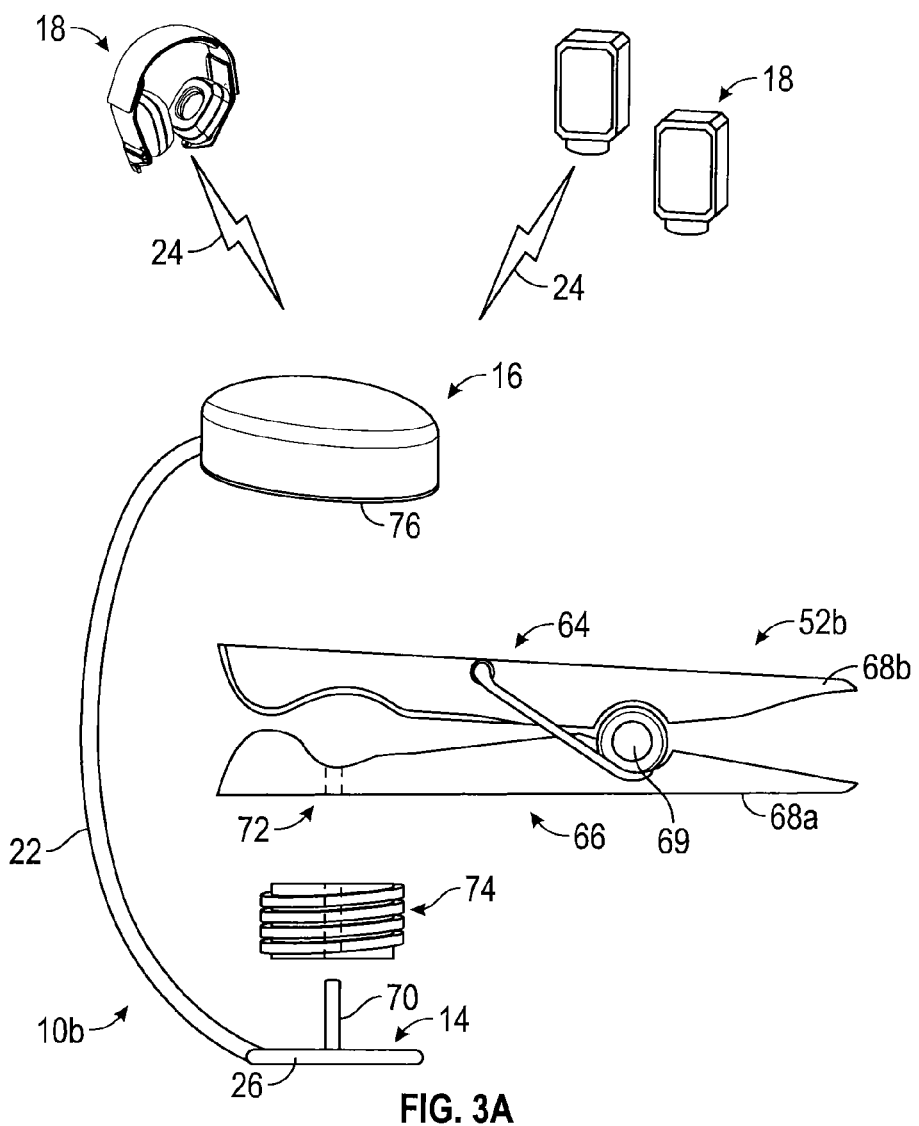
FIG. 3A illustrates a schematic view and FIG. 3B illustrates a side view of another exemplary embodiment of a surgical feedback system in accordance with the present disclosure. A fastener of the surgical feedback system is positioned between an input device and a control unit.
Figure 3B:
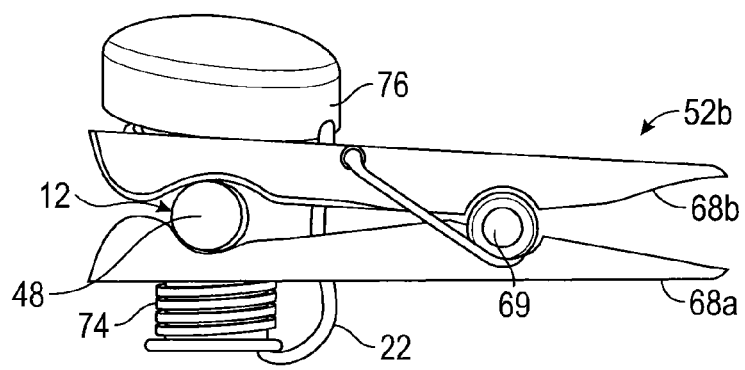

FIGS. 3A and 3B illustrate an exemplary embodiment of a surgical feedback system 10b in accordance with the present disclosure. The surgical feedback system 10b generally may include a fastener 52b positioned between the input device 14 and the control unit 16 for fastening the input device 14 in the control unit 16 to at least a portion of the surgical tool 12. The fastener 52b may include a first end 64 and a second end 66. The input device 14 may be positioned at the first end 64 of the fastener 52b and in communication via the communication link 22 with the control unit 16 positioned at the second end 66 of the fastener 52b.

In some embodiments, the fastener 52b may comprise a plurality of legs 68a and 68b forced together by a spring 69 for causing a portion of the legs 68a and 68b to engage and grip at least a portion of the surgical tool 12, such as the shaft 48. The legs 60a and 60b may be coated with a non-skid material to assist the legs 68a and 68b to grip the surgical tool 12 during use. As the legs 68a and 68b may be spring loaded and adjustable, the fastener 52b may be adjusted during use of the surgical tool 12 and moved to and from different elements (e.g., handle 46, shaft 48) having different widths along the surgical tool 12. FIG. 3B illustrates the fastener 52b gripping the shaft 48 of the surgical tool 12.

The input device 14 may include one or more sensors 26. For example, in FIG. 3A, the sensor 26 includes a contact microphone (e.g., piezo microphone). In addition to the sensor 26, the input device 14 may include one or more acoustic transfer members 70 connected to the sensor 26 and extending from the sensor 26. As shown, the acoustic transfer member 70 extends from the sensor 26 at an angle about normal to an upper surface of the sensor 26 although the acoustic transfer member 70 may extend from the sensor 26 at non-normal angles as well. In the example shown, the sensor 26 is configured to have a flat, disk-shape although it should be understood that other shapes and configurations can be used. The acoustic transfer member 70 may be configured to transfer vibrations from the surgical tool 12 (e.g., shaft 48, handle 46) to the sensor 26. For example, in FIG. 3A, one acoustic transfer member 70 is positioned in contact with the sensor 26 and also positioned in contact with the shaft 48 through an opening 72 in the fastener 52b. In some embodiments, the opening 72 in the fastener 52b may be formed to fit the size and shape of the one or more acoustic transfer members 70. The size and shape of the one or more acoustic transfer members 70 may be determined based on the amount and frequency of the vibration, a desire to not obscure the surgeon's view (e.g., low profile), and an allowance for hand placement along the shaft 48, if desired. The acoustic transfer member 70 may be constructed of one or more solid materials configured to convey acoustic signals, such as a resin or fiber-based material, such as but not limited to fiberglass or carbon fiber, or one or more metallic materials, such as stainless steel or aluminum and combinations thereof.

In some embodiments, a connection assembly 74 may be positioned about the acoustic transfer member 70 to ensure the acoustic transfer member 70 remains in contact with the sensor 26 and the surgical tool 12. The connection assembly 74 may be connected to the second end 66 and the sensor 26 and functions to bias the acoustic transfer member 70 towards the surgical tool 12 to maintain contact between the acoustic transfer member 70 and the surgical tool 12. For example, the connection assembly 74 may include a tensile spring as illustrated in FIGS. 3A and 3B that expands as the sensor 26 is moved away from the end 66. Other materials and configurations may be used for ensuring the acoustic transfer member 70 stays in contact with the sensor 26 and the surgical tool 12 including, but not limited to, foam support, plastic support, and/or the like, for example. In some embodiments, the connection assembly 74 may be attached (e.g., adhesive) to the leg 68a of the fastener 52b and the sensor 26. The acoustic transfer member 70 has a length which exceeds the combined thickness of the connection assembly 74 and the leg 68a (adjacent to the shaft 48) so that an end of the acoustic transfer member 70 extends between the legs 68a and 68b and contacts the shaft 48 when the shaft 48 is positioned between the legs 68a and 68b and at least one of the legs 68a and 68b grip the shaft 48.

The one or more sensors 26 of the input device 14 may be in communication with the control unit 16 via communication link 22. For example, FIGS. 3A and 3B illustrate the sensor 26 in communication with the control unit 16 via a wired communication link 22. Although the wired communication link 22 is illustrated, it should be understood that the communication link 22 may be wired or wireless.

Referring to FIGS. 1 and 3A, the surgical feedback system 10b may also include a housing 76. The housing 76 may support or encompass the control unit 16 and/or one or more power supply(ies). In the example depicted in FIG. 3A, the housing 76 is separate from the sensor 26 and/or the acoustic transfer member 70. The size and shape of the housing 76 may be determined by the size and shape of the control unit 16 and/or the power supply(ies) 20. The housing 76 may be attached (e.g., attached by adhesive) to the leg 68b of the fastener 52b. In some embodiments, the housing 76 may support or encompass the control unit 16 having one or more processors 28 configured to transmit at least one of the original signal and the modified signal (e.g., via Bluetooth) via the communication link 24 to one or more output devices 18 (e.g., headphones, speakers, etc.).

FIGS. 4A and 4B illustrates an exemplary embodiments of a surgical feedback system 10c having a housing 40a. Generally, the housing 40a may include a fastener 52c having one or more legs 78. The one or more legs 78 may be formed to follow the contours of the shaft 48 of the surgical tool 12 when positioned on the shaft 48 of the surgical tool 12 as illustrated in FIG. 4B. In general it is advantageous for the housing 40a to be independent of the surgical tool handle 46. The advantages include ease of sterilization, reusability and the economies of modularization. However, in FIGS. 4A and 4B, the housing 40a could be connected within or be integral to the handle of the surgical tool.

Figure 4D:
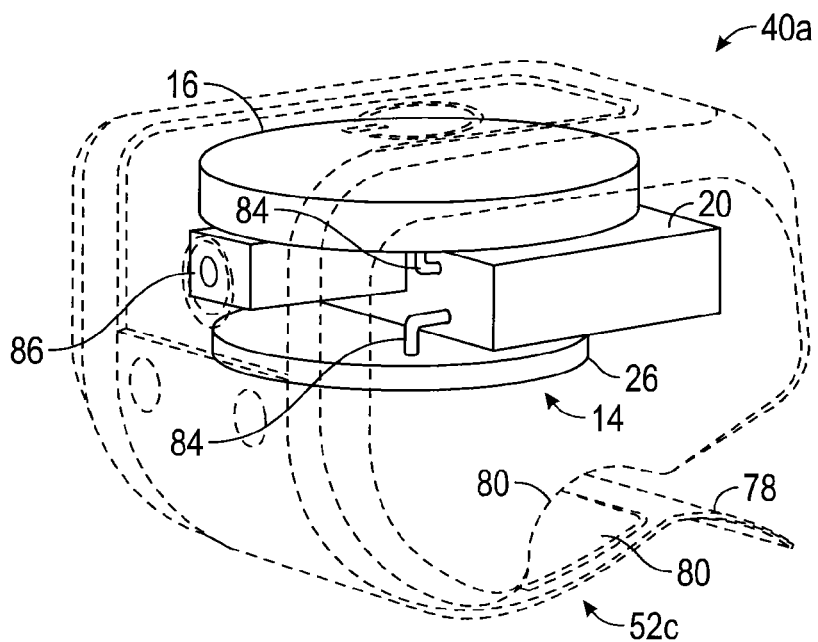

Referring to FIGS. 4C and 4D, the one or more legs 78 may be attached to the housing 40a and configured to grip the shaft 48 by providing a bias, such as a constant spring-force, to press the shaft 48 against the housing 40a. In some embodiments, at least one of the housing 40a and the leg 78 may include a gripping surface 80. The gripping surface 80 maybe formed of material including, but not limited to silicon, or any other material capable of aiding in gripping of the shaft 48 during use. In the example shown, the gripping surface 80 is provided on the leg 78 and positioned to engage the shaft 48 to prevent the shaft 48 from slipping relative to the leg 78.

In some embodiments, the leg 78 and/or housing 40a may be formed of material (e.g., non-cushioning and non-gripping) configured to pass vibrations from the surgical tool 12 to the input device 14 with a minimum amount of attenuation. In the example shown, the housing 40a, rather than the leg 78, is formed of material configured to pass vibrations from the surgical tool 12 to the input device 14, such as a generally rigid sound transferring materials including but not limited to stainless steel, aluminum, titanium, ceramics and polymers including but not limited to polyphenylsulphone, Acrylonitrile butadiene styrene (ABS), and Polyether ether ketone (PEEK) and others.

Referring to FIGS. 1 and 4D, the housing 40a may support or encompass the input device 14, the control unit 16, and the power supply 20. In some embodiments, the housing 40a may also support or encompass the output device 18. For example, the output device 18 may be a speaker positioned on or within the housing 40a and configured to transmit the modified signal to the surgeon or operating environment.

Referring to FIGS. 4B and 4D, the input device 14 may include one or more sensors 26, such as but not limited to a contact microphone. In some embodiments, a portion 82 of the housing 40a (or a separate member embedded within the housing) may serve as an acoustic transfer member, as described herein, that engages the one or more sensors 26 and the shaft 48 of the surgical tool 12 to pass acoustic vibrations from the shaft 48 to the one or more sensors 26.

Referring to FIGS. 1 and 4D, in some embodiments, the power supply 20 for the input device 14, control unit 16, and/or output device 18 may be connected via one or more lines 84. For example, FIG. 4D illustrates a power connector port 86 for providing power via one or more lines 84 to at least the input device and the control unit 16. Additionally, power to the input device 14, control unit 16 and/or output device 18 may be controlled via a power switch 87 located on an exterior surface of the housing 40a.

Figure 5A:
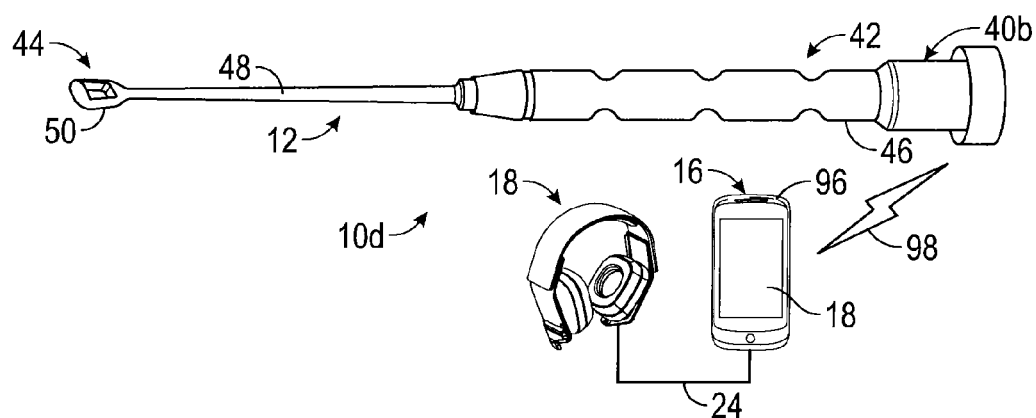
FIG. 5A illustrates a side view another exemplary embodiment of a surgical feedback system in accordance with the present disclosure. The surgical feedback system includes a housing configured to be permanently attached to a surgical tool.
Figure 5B:
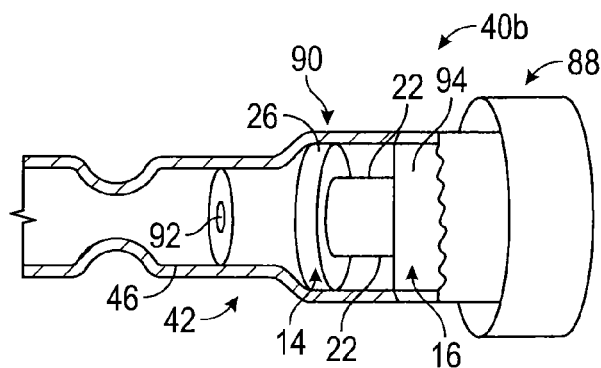
FIG. 5B illustrates a partially cutaway side view of the housing of the surgical feedback system and the handle of the surgical tool of FIG. 4A.

FIGS. 5A and 5B illustrate an exemplary embodiment of a surgical feedback system 10d having one or more sensors 26 supported or encompassed within a housing 40b. The housing 40b may be permanently or removably attached to the surgical tool 12. FIG. 5A illustrates an exemplary embodiment wherein the housing 40b is permanently attached to the proximal end 46 of the surgical tool 12.

The housing 40b may have a proximal end 88 and a distal end 90. The distal end 90 of the housing 40b may attach to the handle 46 at the proximal end 42 of the surgical tool 12. Attachment of the handle 46 to the housing 40b may be implemented in a manner that transfers soundwaves from the handle 46 to the housing 40b with minimal loss or noise. Exemplary implementations may include, but are not limited to, compression fit, threaded attachment, screw-in, lock and key, and/or the like.

The one or more sensors 26 may be positioned at the distal end 90 of the housing 40b. In some embodiments, the distal end 90 of the housing 40b may include one or more openings 92. The one or more openings 92 may provide for one or more unobstructed pathway for signals (e.g., acoustic signals) to travel from the handle 46 to the sensor 26. In some embodiments, the handle 46 of the surgical tool 12 may include a hollow interior as shown in FIG. 5B. Even further, in some embodiments, the sensor 26 is a contact microphone contacting the shaft 48 of the surgical tool 12 to sense audio vibrations through the shaft 48 of the surgical tool.

The one or more sensors 26 may communicate with the control unit 16 via one or more communication links 22 as shown in FIG. 5B. In some embodiments, the control unit 16 or a portion of the control unit 16 may be supported or encompassed by the housing 40*b*. As illustrated in FIGS. 5A and 5B, a first portion 94 of the control unit 16 is supported by the housing 40*b*, and a second portion 96 of the control unit 16 is external to the housing 40*b*. The first portion 94 of the control unit 16 may communicate with the second portion 96 of the control unit 16 via a communication link 98. The communication link 98 may be wired or wireless and similar to embodiments described in relation to communication links 22 and 24 as discussed herein. To that end, in some embodiments, the communication link 98 may communicate with a network (e.g., cloud-based).

Figure 5C:
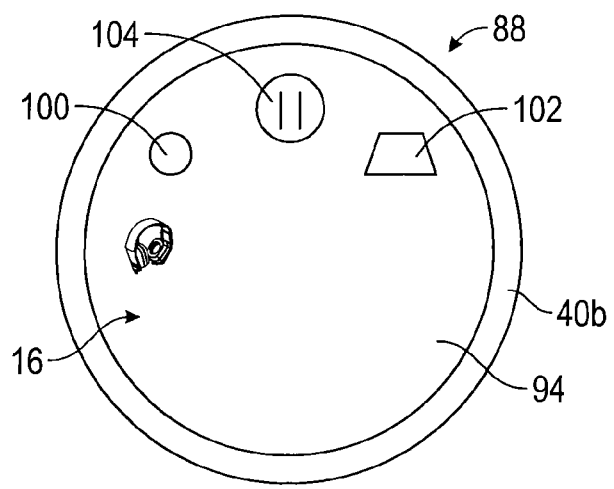
FIG. 5C illustrates a side view of an exemplary proximal end of the housing of the surgical feedback system of FIG. 4A having a plurality of ports for communication with other elements of the surgical feedback system.

In some embodiments, the first portion 94 of the control unit 16 may provide the modified signal to the output device 18. For example, FIG. 5C illustrates an outlet port 100 for implementing the communication link 24 between the control unit 16 and output device 18. In some embodiments, the output device 18 may include headphones plugged into the outlet port 100.

In some embodiments, the first portion 94 of the control unit 16 may provide a first modified signal to the second portion 96 of the control unit 16 via the communication link 98. For example, FIG. 5C illustrates a connection port 102 for the communication link 98 for a wired connection between the first portion 94 of the control unit 16 and the second portion 96 of the control unit 16. It should be noted that additional portions of the control unit 16 are contemplated with one or more communication links. Also, although the connection port 102 is for a wired connection, the communication link 98 may be wired, wireless, or a combination thereof, as described further herein.

The second portion 96 of the control unit 16 may further modify the signal, store the further modified signal, store the modified signal provided by the first portion 94, communicate the modified signal and/or further modified signal to one or more output device 18, and/or the like. For example, in some embodiments, the first portion 94 of the control unit 16 may provide the modified signal to one or more output devices 18 and also provide the modified signal to the second portion 96 of the control unit 16. In this example, a surgeon may be able to process the modified signal (e.g., hear, visualize) via one or more output devices 18, while the second portion 96 of the control unit 16 may further process or record the modified signal to evaluate and/or determine best practice for future surgeries, for example. Additionally, the second portion 96 of the control unit 16 may provide the modified signal and/or further modified signal to one or more output devices 18. For example, in FIG. 5A, the second portion 96 of the control unit 16 is providing the modified signal and/or the further modified signal to two different output devices 18: headphones and a display screen of a smart device.

Referring to FIGS. 1 and 5C, in some embodiments, the power supply 20 for the input device 14, control unit 16, and/or output device 18 may be connected via the one or more lines 84. For example, FIG. 5C illustrates a power connector port 104 for providing power via one or more lines 84 to the first portion 94 of the control unit 16 and the sensor 26 of the input device 14.

Figure 5D:
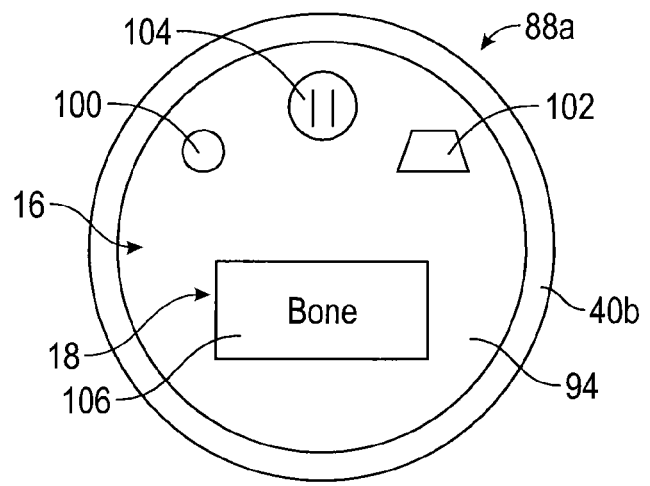
FIG. 5D illustrates a side view of another exemplary proximal end of the housing of the surgical feedback system of FIG. 4A having a display screen for transmitting a modified signal to a surgeon or operating environment.

FIG. 5D illustrates an exemplary embodiment of a proximal end 88*a* of the housing 40*b* for use with the surgical tool 12 of FIG. 5A, wherein at least one output device 18 is positioned on the proximal end 88*a* of the housing 40*b* for visual display of the modified signal. Similar to FIG. 5B, the proximal end 88*a* may include the output port 100 for one or more output devices 18, the connection port 102 for communication with one or more portion of the control unit 16 and/or to supply power to deliver charge to internal rechargeable batteries, and/or the power connector port 104 for supplying power. The proximal end 88*a* may further include one or more output devices 18 having a display 106. The display 106 may provide one or more image or data indicators using modes of data including, but not limited to, numeric, alphanumeric, byte/binary, and/or the like. For example, in some embodiments, the control unit 16 may direct the display 106 to provide a first color for detected signals having a first frequency and/or intensity, and a second color for detected signals having a second frequency and/or intensity. In another example, as illustrated in FIG. 5D, the control unit 16 may direct the display 106 to provide the alphanumeric word "BONE" when the control unit 16 determines the original signal is at a frequency and/or intensity wherein the surgeon is in contact with bone using the surgical tool 12.

Figure 5E:
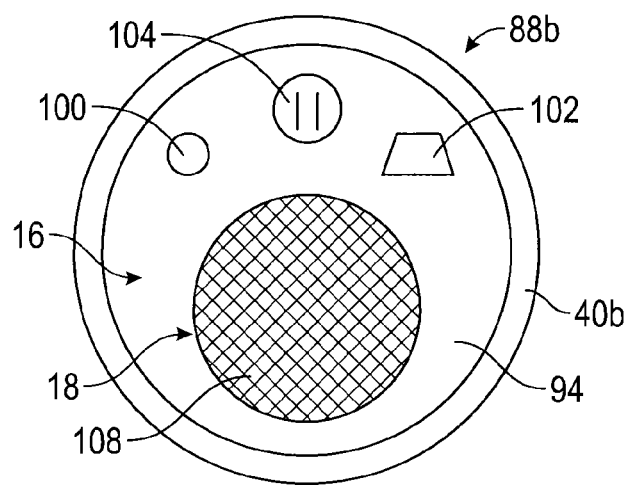
FIG. 5E illustrates a side view of another exemplary proximal end of the housing of the surgical feedback system of FIG. 4A having a speaker for transmitting a modified signal to a surgeon or operating environment.

FIG. 5E illustrates another exemplary embodiment of a proximal end 88*b* of the housing 40*b* for use with the surgical tool 12 of FIG. 5A, wherein the proximal end 88*b* includes at least one output device 18 for audio broadcast of the original signal and/or the modified signal. In this example, the output device 18 may include a speaker 108 in communication with the control unit 16 or in direct communication with the input device 14 (not shown in FIG. 5E).

Figure 6:
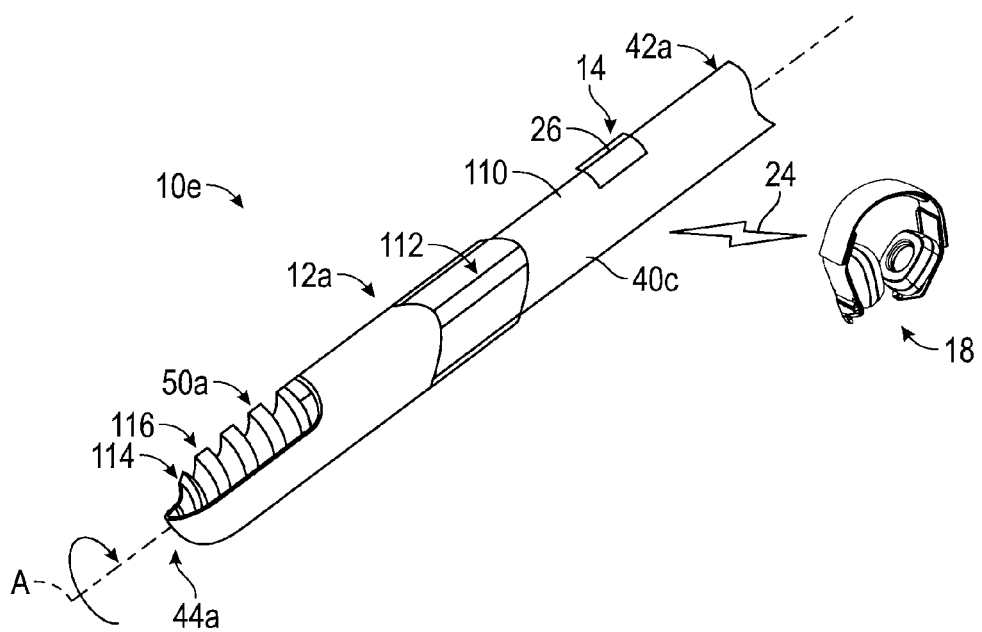
FIG. 6 illustrates a schematic view of another exemplary embodiment of a portion of a surgical feedback system in accordance with the present disclosure. The Figure including a partially cutaway view of an interior of a surgical tool.

FIG. 6 illustrates another exemplary embodiment of the surgical feedback system 10*e*. The input device 14 may be positioned on an external surface 110 of a surgical tool 12*a*. A distal end 44*a* of the surgical tool 12*a* may include a functional tool 50*a*. The functional tool 50*a* may include a shaft 112 and a distal end 114.

The shaft 112 of the functional tool 50*a* may be supported or encompassed by the housing 40*c*. The distal end 114 of the functional tool 50*a* may include a functional tip 116. For example, the functional tip 116 may include a bit capable of rotation about an axis A. Rotation of the bit about the axis A may allow the bit to cut through biological material including, but not limited to, tissue, bone, and/or the like. As one skilled in the art will appreciate, the configuration, shape and size of the functional tip 116 may be based on the intended use of the functional tool 50*a* during a surgical procedure.

Referring to FIGS. 1 and 6, in some embodiments, the control unit 16 may control the functional tool 50*a* of the surgical tool 12*a*. For example, the control unit 16 may be configured to determine, using original signals provided by one or more sensors 26, what type of biological material (e.g., bone) the functional tip 116 may be in contact with. To that end, in some embodiments, the control unit 16 may be configured to stop functionality (e.g., rotation of the bit) of the tool 50*a* and/or tip 116 based on the type of biological material the tool 50*a* and/or tip 116 may be in contact with as determined by the control unit 16 and described in further detail herein.

Generally, feedback may be provided by the control unit 16 to any component of the surgical tool 12*a* that modulates functionality (e.g., cutting effectiveness). For example, feedback provided by the control unit 16 may move the functional tip 116 (e.g., a cutting element that may be spinning, oscillating, vibrating) of the functional tool 50*a* to modulate cutting effectiveness. In another example, an active mechanically based force transmission element that is mechanically, optically, chemically, magnetically, or electronically controlled may modulate cutting effectiveness by shutting down the functional tool 50*a*. In another example, one or more shielding apparatus may be moved from a first location exposing the functional tool 50*a* to a second location covering the functional tool 50a to separate the functional tool 50a from the patient's tissue. The shielding apparatus may be mechanically, optically, chemically, magnetically, or electronically controlled to modulate cutting effectiveness. In another example, the functional tip 116 may be retracted into the housing 40c to modulate cutting effectiveness.

In some embodiments, the control unit 16 may shut off power to the surgical tool 12a ceasing rotation, lateral movement (or other types of movement) of the functional tip 116, de-actuate a motor or other type of device causing the functional tool 50a to move, and/or the like, for example. Alternatively, the control unit 16 may be configured to initiate functionality of tool 50a and/or the tip 116 based on input received by the control unit 16. For example, a surgeon may provide a voice command to the control unit 16 to initiate functionality (e.g., resume rotation).

Figure 7A:
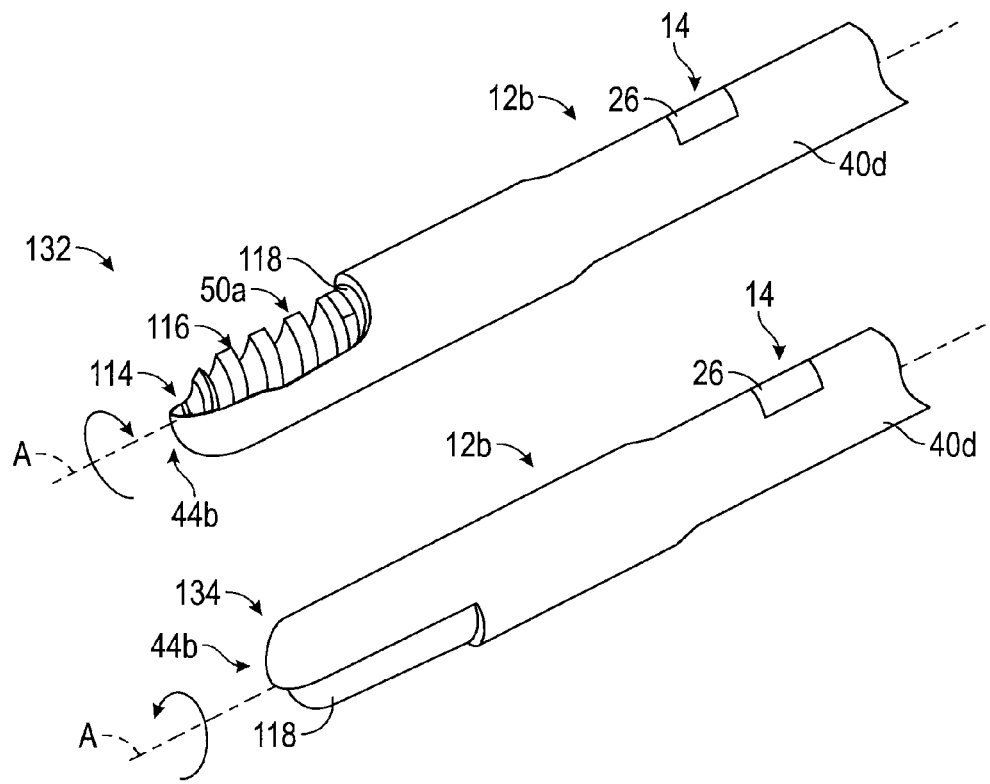
FIG. 7A illustrates a perspective view of another exemplary embodiment of a portion of a surgical feedback system in accordance with the present disclosure. The surgical feedback system is illustrated in two positions. In a first position, a functional tip of a surgical tool is visible. In a second position, a shield covers the functional tip of the surgical tool in response to a modified signal transmitted by a control unit of the surgical feedback system.
Figure 7B:
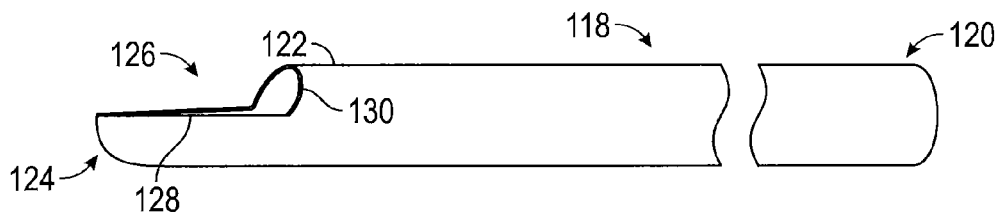
FIG. 7B illustrates a perspective view of an exemplary shield for use in the surgical feedback system illustrated in FIG. 6A.

FIGS. 7A and 7B illustrate another exemplary embodiment, wherein the functionality of a surgical tool 12b may be controlled by the control unit 16 illustrated in FIG. 1. It should be noted that the control unit 16 may be supported or encompassed by a housing 40d of the surgical tool 12b, one or more portions may be supported or encompassed by housing 40d of the surgical tool 12b, or the control unit 16 may be positioned within the operating environment and communicate with the sensors 26 and components of the functional tool 50a via a network as described in further detail herein.

Referring to FIGS. 1 and 7A-7B, generally, the surgical tool 12b may include a shield 118 positioned adjacent to the functional tip 116 of the functional tool 50a of the surgical tool 12b. An actuator 117 connected to the shield 118 may be configured to move the shield from a first position 132 to expose the functional tool 50a, to a second position 134 to cover the functional tool 50a. In some embodiments, the control unit 16 (shown in FIG. 1) may transmit a signal to the actuator 117 of the surgical tool 12b to move the shield 118 to the first position 132 or the second position 134 to cover or uncover the functional tip 116, respectively.

As illustrated in FIGS. 7A and 7B, the shield 118 may be capable of rotation about an axis A. FIG. 7B illustrates an exemplary embodiment of the shield 118. The shield 118 may have a proximal end 120 and a sidewall 122 extending towards a distal end 124. In some embodiments, the sidewall 122 may extend the length of the housing 40d illustrated in FIG. 7A. Alternatively, the sidewall 122 may extend a portion of the length of the housing 40d.

The sidewall 122 of the shield 118 may extend the length L of the housing 40d to a distal end 44b of the housing 40d. The sidewall 122 may include an opening referred to herein as an exposed portion 126 having a first side 128 and a second side 130 with the first side 128 intersecting the second side 130. The sidewall 122 may define a hollow interior space formed such that the functional tip 116 of the functional tool 50a may fit within the hollow interior of the shield 118 during use.

Referring to FIG. 7A, during use of the functional tool 50a, the shield 118 may be positioned at a first position 132 such that a functional tip 116 at a distal end 44b of the housing 40d may be exposed. The control unit 16 may be configured to signal the surgical tool 12b to rotate the shield 118 about the axis A to a second position 134 upon determination that the functional tip 116 is in contact with a pre-determined biological material (e.g., bone, tissue). In some embodiments, the functional tip 116 may continue to rotate about the axis A with the shield 118 in the second position 134.

Figure 8:
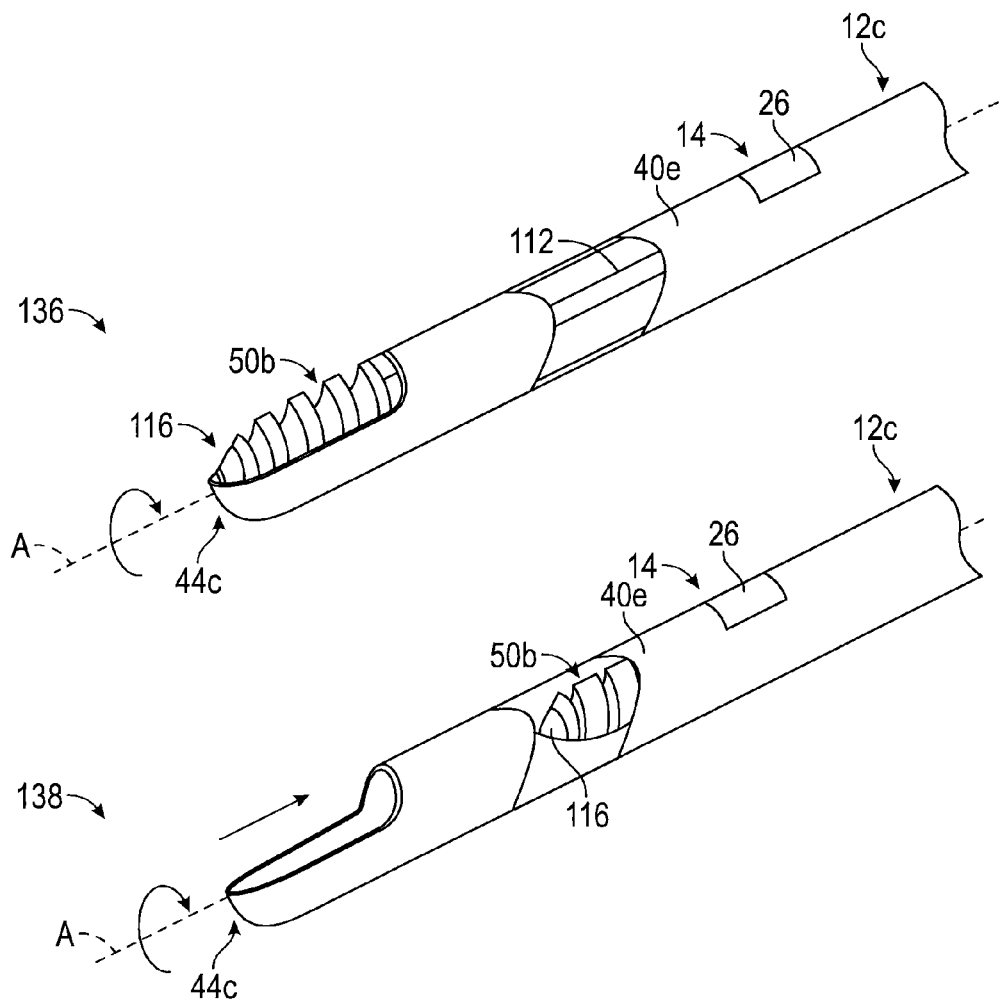
FIG. 8 illustrates another exemplary embodiment of a portion of a surgical feedback system in accordance with the present disclosure. The surgical feedback system illustrated in two positions. In a first position, a functional tip of a surgical tool is visible. In a second position, the functional tip of the surgical tool is retracted inside an interior of the surgical tool in response to a modified signal transmitted by a control unit of the surgical feedback system.

FIG. 8 illustrates another exemplary embodiment, wherein the functionality of a surgical tool 12c may be altered by signals transmitted by the control unit 16 illustrated in FIG. 1. The control unit 16 may be supported or encompassed by a housing 40e of the surgical tool 12c, one or more portions may be supported or encompassed by housing 40e of the surgical tool 12c, or the control unit 16 may be positioned within the operating environment and communicate with the sensors 26 and mechanics of a functional tool 50b via a network as described in further detail herein.

Referring to FIGS. 1 and 8, generally, the functional tip 116 positioned at a distal end 44c of the housing 40e may be configured to be selectively retracted by the actuator 117 (see FIG. 1) of the surgical tool 12c (using a spring or threaded mechanism, for example) to limit the ability of the functional tip 116 to contact the patient's tissue. For example, the functional tip 116 of the functional tool 50c may rotate about the axis A during use in a first position 136, with the functional tool 50b using the functional tip 116 to cut into a first tissue type or surface type. The control unit 16 may determine that the functional tip 116 is in contact with a second tissue type or surface type different from the first tissue type or surface type. The control unit 16 may signal to the surgical tool 12c, functional tool 50b, and/or a user to retract the functional tip 116 into the housing 40e (e.g., using a spring or threaded mechanism) such that the functional tool 50b is in a second position 138. Retraction of the functional tip 116 may provide selectively in cutting of soft tissues and/or bone, for example.

In one example, retraction of the functional tip 116 of the functional tool 50b may be actuated by a surgeon by pressing a button, for example to send a signal to the actuator 117, which may be connected to the functional tip 116 to cause the actuator 117 to retract the functional tip 116. In other embodiments, the functional tip 116 may be retracted by the surgeon moving the housing 40e relative to the functional tip 116. The surgeon may receive the modified signal via the output device 18 as discussed with reference to FIG. 1. Upon receiving the modified signal, the surgeon may retract the functional tip 116 of the functional tool 50b within the housing 40e.

Figure 9:
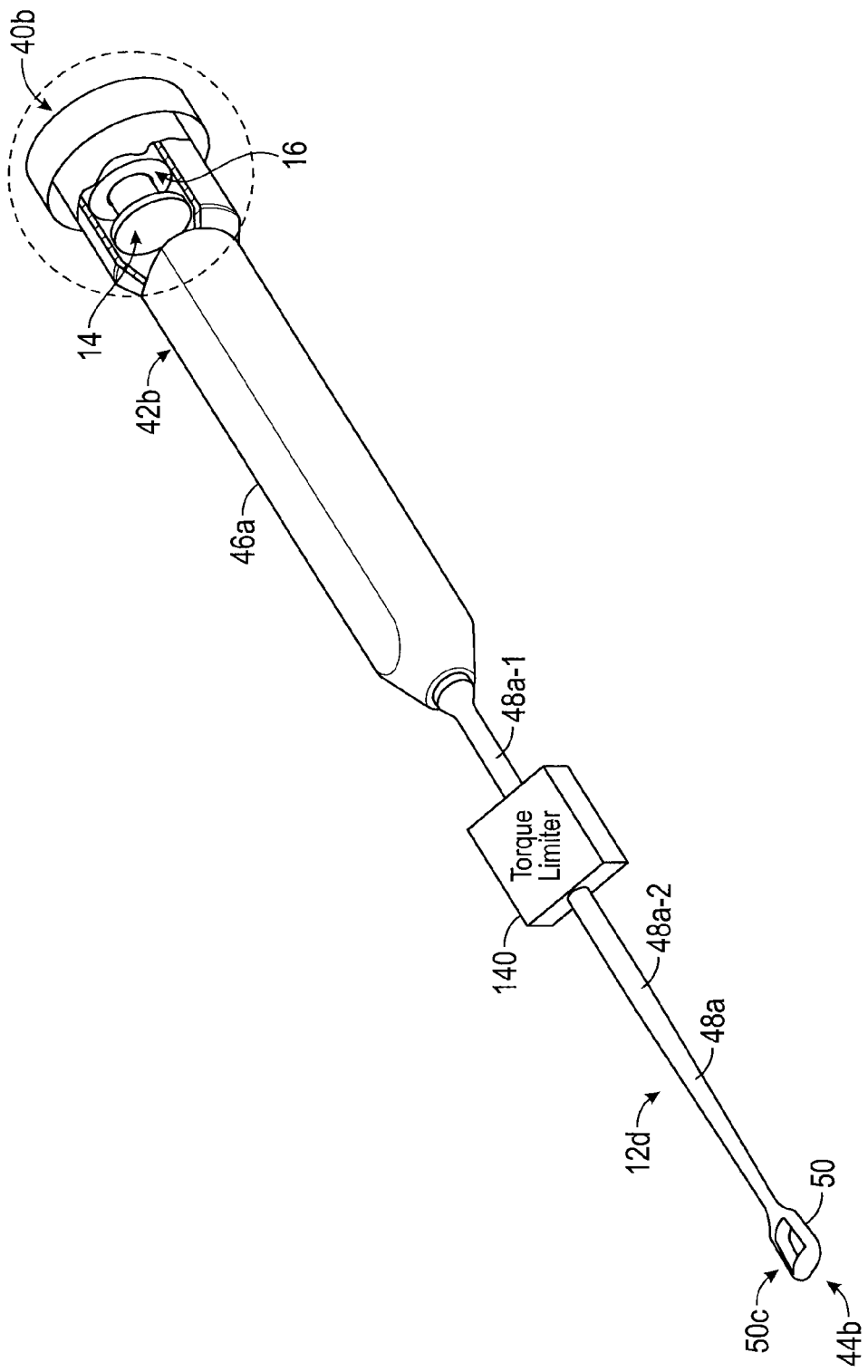
FIG. 9 illustrates a perspective, partial sectional and partial schematic view of another exemplary surgical tool wherein the amount of force applied from a handle positioned at a proximal end of the surgical tool to a functional tool positioned at a distal end may be controlled. In particular, the surgical tool of FIG. 9 includes a torque limiter that is shown in schematic form for regulating the amount of force applied to the functional tool.

FIG. 9 illustrates another exemplary embodiment of a surgical tool 12d wherein the amount of force applied from a handle 46a positioned at a proximal end 42b of the surgical tool 12d to a functional tool 50c positioned at a distal end 44b may be controlled. Generally, the surgical tool 12d may include the handle 46a connected to a shaft 48a with the functional tool 50c similar to the surgical tool 12 illustrated in FIG. 2. The surgical tool 12d may include a torque limiter 140 generally between the handle 46a and the functional tool 50c. In some embodiments, the torque limiter 140 may be positioned at a distal end 44 of the surgical tool 12d. In FIG. 9, the shaft 48a is provided with a first segment 48a-1 and a second segment 48a-2. The first segment 48a-1 is connected to the handle 46a and the second segment 48a-2 is connected to the functional tool. The torque limiter 140 is positioned between the first segment 48a-1 and the second segment 48a-2 and movably connects the first segment 48a-1 to the second segment 48a-2.

Generally, the torque limiter 140 permits the handle 46a and the functional tool 50c to move relative to each other based on the amount of force(s) applied to the handle 46a by a surgeon and/or the amount of force applied by the functional tool 50c. The torque limiter 140 positioned between the handle 46a and the functional tool 50c may limit the amount of force applied to the functional tool 50c by having two or more members which slip or uncouple relative to each other. Exemplary torque limiters 140 may include, but are not limited to, ball and detents, clutches, friction plates, magnets and/or the like. In some embodiments, the torque limiter 140 is provided with an actuator (not shown) and the control unit 16 may provide a signal to the actuator 140 of the torque limiter 140 to cause the two or more members of the torque limiter 140 to slip or uncouple thus limiting the amount of force applied to the functional tool 50*c*. Additionally, in some embodiments, other systems may be used to track the amount of load applied to the shaft 48*a*. For example, a wheatstone bridge, strain gauge, sensor, and/or the like may be coupled to the control unit 16 to permit the control unit 16 to track the amount of load applied to the shaft 48*a* and to generate and send control signals to the torque limiter 140 to cause the torque limiter to slip or uncouple when the amount of force exceeds a predetermined baseline, or to limit the cutting effectiveness of the functional tool 50*c* based upon the type of tissue that the functional tool 50*c* is contacting.

Figure 10:
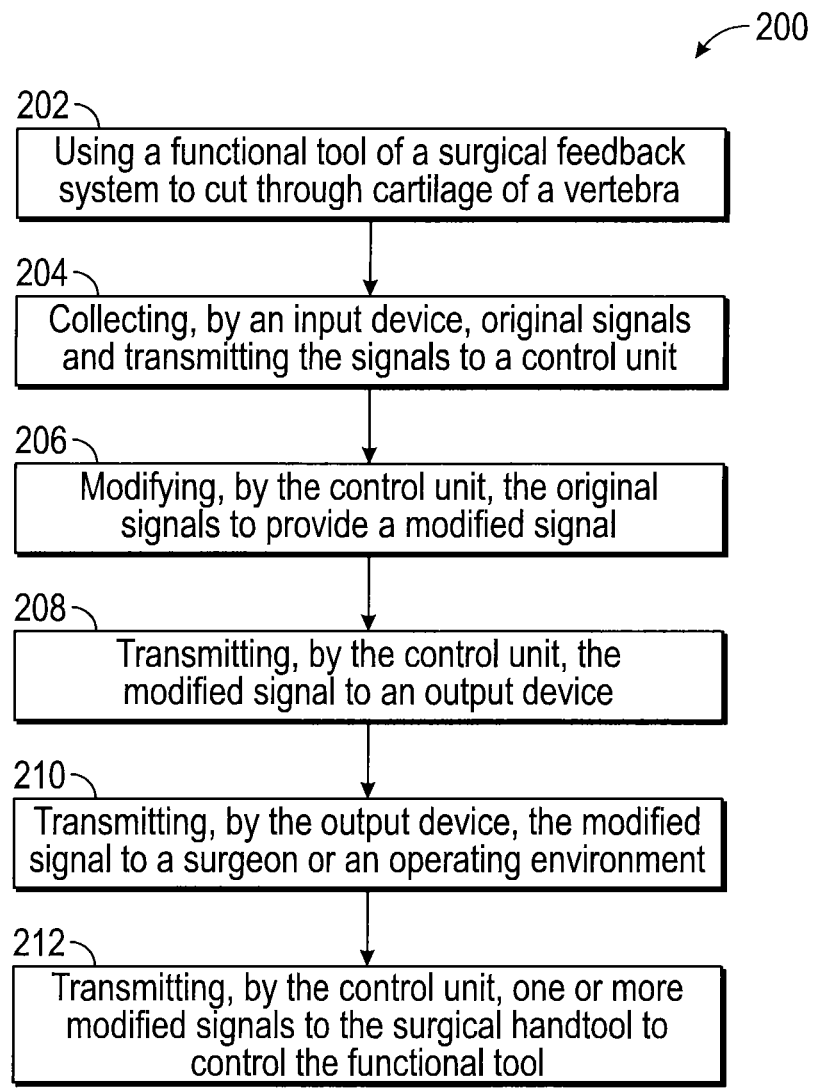
FIG. 10 illustrates a flow chart of an exemplary method for using a surgical feedback system during a surgical procedure.

FIG. 10 illustrates a flow chart 200 of an exemplary method for using the surgical feedback system 10 during a surgical procedure. In particular, the method describes the use of the surgical feedback system 10 during vertebral body endplate preparation. In some embodiments, the functional tool 50 of the surgical tool 12 may include a rasp. Generally, using the surgical feedback system 10, the rasp may remove a cartilage layer and prepare a cavity or surface in the endplate without causing excessive damage to the cancellous endplate of the vertebrae.

Prior to use of the surgical feedback system, a skin incision may be made and subcutaneous tissue taken down such that the oblique muscles of the abdomen of the patient may be visible. An operative corridor to the patient's spine may be formed through the oblique muscles, retroperitoneal space, and the psoas muscle. The operative corridor may be formed by advancing a K-wire and dilator towards a target site, for example. In some embodiments, an obturator may be included inside the dilator. Once the proper location is determined, the K-wire may be inserted down the center of the dilator and docked at an annulus of an intervertebral disc. Dilators of increasing diameter may then be guided over the previously installed dilator until a desired lumen is provided. A working dilator may then be installed to establish the operative corridor there through. The surgeon may then prepare the endplates of the patient's spine using the surgical feedback system 10.

In a step 202, the functional tool 50 of surgical tool 12 of the surgical feedback system 10 may begin cutting through cartilage of a vertebra. In a step 204, one or more sensors 26 may collect one or more original signals and transmit the original signals to the control unit 16. For example, an acoustic microphone (i.e., sensor 26) may collect one or more original signals and transmit the original signal wirelessly via a suitable protocol such as Bluetooth to a smart phone (i.e., control unit 16). In a step 206, the control unit 16 may evaluate and modify the original signal to provide a modified signal. For example, the control unit 16 may modify the original signal by amplifying the signal or shift the signal frequency to be optimized for human hearing (e.g., 5 Hz-20 kHz). In a step 208, the control unit 16 may transmit the modified signal to the output device 18. For example, the smart phone (i.e., control unit 16) may transmit an amplified signal to headphones worn by the surgeon. In a step 210, the output device 18 may transmit the modified signal to the surgeon and/or operating environment. In a step 212, the control unit 16 may transmit one or more modified signals to the surgical tool 12 to control the functional tool 50 of the surgical tool 12. For example, the control unit 16 may transmit one or more modified signals to the surgical tool 12 instructing the surgical tool 12 to cease power to the functional tool 50. To that end, cutting, or other functionality of the functional tool 50, may cease.

What is claimed is:

1. A surgical feedback system, comprising:
    a surgical tool having a proximal end and a distal end, the proximal end having a functional tool and the distal end having a handle for manipulation by a surgeon in a surgical environment;
    a housing connected to a portion of the surgical tool, the housing supporting at least one sensor configured to generate a first signal indicative of at least one of an acoustic signal or a vibration signal generated by the functional tool, the at least one sensor being tuned to eliminate known acoustic and/or vibration noise within a surgical area;
    at least one output device; and
    a control unit receiving the first signal and supplying at least one of the first signal and a modified signal based on the first signal to the at least one output device.

2. The system of claim 1, wherein the housing includes a fastener configured to removably attach the housing to the surgical tool.

3. The system of claim 1, wherein the surgical tool has a shaft connecting the functional tool to the handle, and wherein the housing is attached to the shaft of the surgical tool.

4. The system of claim 1, wherein the at least one sensor is a contact microphone configured to sense audio vibrations within the surgical tool and generate electrical signals indicative of the audio vibrations.

5. The system of claim 1, wherein the at least one sensor further comprises a wireless transmitter and wherein the control unit further comprises a wireless receiver configured to communicate with the wireless transmitter.

6. The system of claim 1, wherein the control unit includes at least one processor coupled to at least one memory and configured to communicate with the sensor, the memory being a non-transitory memory having processor executable code stored therein that when executed by the processor cause the processor to modify the first signal to provide the modified signal.

7. The system of claim 6, wherein the output device is a display screen supported by the housing, and the modified signal is at least one of a text or graphical display.

8. The system of claim 6, wherein the processor executable code when executed by the processor cause the processor to further:
    analyze the first signal; and,
    determine a tissue type or surface type in contact with the functional tool based on the first signal.

9. The system of claim 8, wherein the modified signal transmitted by the output device includes at least one of the tissue type or surface type.

10. The system of claim 8, wherein the processor executable code when executed by the processor cause the processor to further transmit a signal that is received and interpreted by a component that functions to cease movement of the functional tool of the surgical tool.

11. The system of claim 8, wherein determining the tissue type or surface type in contact with the functional tool is defined further as analyzing and receiving a positive indication in a first frequency band and a second frequency band in the first signal to determine the tissue type or surface type in contact with the functional tool.

12. The system of claim 1, wherein the surgical tool further comprises a shaft positioned between the functional tool and the handle.

13. The system of claim 12, wherein the housing is positioned on the shaft.

14. A kit, comprising:
 a surgical feedback system comprising:
  an input device with at least one sensor configured to collect a plurality of original signals, the plurality of original signals having at least one of an acoustic signal or a vibration signal, the input device including a clip having at least two legs;
  a control unit configured to receive the original signals from the input device and modify the signals providing a modified signal configured to notify a surgeon of a type of tissue being contacted by the input device;
  an output device configured to receive the modified signal and transmit the modified signal;
 a surgical tool having a handle and a shaft and at least two widths along the surgical tool; and
 wherein the legs are spring-loaded and adjustable during use so as to be moved to and from at least one of the handle and the shaft so as to grip differing widths of the surgical tool.

15. The kit of claim 14, wherein the input device includes a microphone, the control unit includes an amplifier, and the output device includes at least one speaker configured to emit audio signals having a frequency within a range from 5 Hz to 20 kHz.

16. The kit of claim 15, wherein the output device is configured to be located within an operating room environment.

17. The kit of claim 14, wherein communication between at least one of the input device, control unit or output device includes wireless communication.

* * * * *